(12) United States Patent  
Appelt et al.

(10) Patent No.: US 7,541,806 B2  
(45) Date of Patent: Jun. 2, 2009

(54) METHOD FOR MOLECULE EXAMINATION BY NMR SPECTROSCOPY

(75) Inventors: Stephan Appelt, Aachen-Soers (DE); Holger Kuhn, Leverkusen (DE); Ulrich Sieling, Erkelenz (DE); Friedrich-Wolfgang Hasing, Julich (DE)

(73) Assignee: Forschungszentrum Julich GmbH, Julich (DE)

( * ) Notice: Subject to any disclaimer, the term of this patent is extended or adjusted under 35 U.S.C. 154(b) by 0 days.

(21) Appl. No.: 11/681,331

(22) Filed: Mar. 2, 2007

(65) Prior Publication Data

US 2007/0296412 A1 Dec. 27, 2007

(30) Foreign Application Priority Data

Jun. 24, 2006 (DE) .................. 10 2006 029 038  
Jul. 14, 2006 (DE) .................. 10 2006 032 855

(51) Int. Cl.  
*G01V 3/00* (2006.01)

(52) U.S. Cl. ..................................... 324/303; 324/307

(58) Field of Classification Search .................. 324/303, 324/307  
See application file for complete search history.

(56) References Cited

U.S. PATENT DOCUMENTS 6,815,950 B2 * 11/2004 Speier .................... 324/303  
6,958,604 B2 * 10/2005 An et al. .................. 324/303

* cited by examiner

*Primary Examiner*—Louis M Arana  
(74) *Attorney, Agent, or Firm*—Rankin, Hill & Clark LLP

(57) ABSTRACT

The invention relates to a method and a device for examining molecules by means of NMR spectroscopy. It is the object of the invention to be able to characterize a sample with a high resolution and comprehensively. The object is solved by a method and an associated device for examining a sample by means of nuclear magnetic spectroscopy by measuring heteronuclear and homonuclear J-couplings in a small magnetic field and by using the measured heteronuclear and homonuclear J-couplings for characterizing the sample.

22 Claims, 13 Drawing Sheets

Example 1:
Tetramethylsilane (TMS)

$A = {}^{13}C,\quad X = {}^{1}H,\quad M = 3$ $B = {}^{12}C - Si - {}^{12}C,\quad X = {}^{1}H,\; K = 9$
$\qquad\quad\;\;|$
$\qquad\;\;{}^{12}C$

| | | | | | | |
|---|---|---|---|---|---|---|
| 1 | Sample tube | 4 | Homogeneous magnet | 7 | Receiving coil | 10 | Magnetic screening |
| 2 | Halbach magnet 1 - 3 T | 5 | Magn. field $B_0 \sim 0 - 50$ G $\Delta B_0/B_0 \sim 1$ ppm | 8 | Transmitting coil | 11 | Hyperpolarization-technologies SEOP (Xe, $^3$He) PHIP ($^{13}$C) SEOP + SPINOE (Xe - $^1$H) |
| 3 | Transport of sample | 6 | Current stabilizer Stability better than 1 ppm | 9 | NMR electronics 200 Hz – 300 kHz | | |

METHOD FOR MOLECULE EXAMINATION BY NMR SPECTROSCOPY

This application claims priority to and incorporates by reference German Application No. 102006029038.0 filed Jun. 24, 2006 and German Application No. 102006032855.8 filed Jul. 14, 2006.

The invention relates to a method and a device for examining molecules by means of NMR spectroscopy.

Nuclear magnetic spectroscopy (NMR) as well as magnetic resonance tomography (MRT) are very successful non-destructive examination methods both for the elucidation of the structure of molecules as well as for imaging matter or living systems. The great successes of NMR and MRT in the last 20 years are reflected by three Nobel prizes that have been awarded (Richard Ernst 1991, Kurt Wüthrich 2002, Paul Lauterbur and Peter Mansfield, 2003). The structural elucidation of macromolecules and of biomolecules by high-resolution or multidimensional NMR spectroscopy, especially, has progressed greatly. Basically, five interactions may be observed in NMR. They consist of:

1. the nuclear Zeeman interaction,
2. the electric nuclear quadrupole interaction
3. the dipole-dipole interaction,
4. the chemical shift, and
5. the J-coupling.

The final three interactions play an important role in the structural elucidation of molecules. For example, the polarization transfer between different nuclei is exploited through the mechanism of dipolar cross-relaxation (nuclear Overhauser-effect spectroscopy, NOESY) for structural elucidation of large molecules. The 2D COSY method employs chemical shift as well as J-coupling in order to measure the network of J-coupled nuclear spins and thus, the molecular structure, as is apparent from the printed publication "Ernst, R. R., Bodenhausen, G. & Wokaun, A. Principles of Nuclear Magnetic Resonance in One and Two Dimensions (Clarendon Press, Oxford, UK, 1987)".

The chemical shift is caused by the fact that a magnetic field $B_0$ produces circular currents through the electrons of a molecule, and thus generates an additional magnetic field of the size $\Delta B = \sigma B_0$ at every position of the observed nuclear spin. This additional magnetic field is proportional to the magnetic field $B_0$ and shifts the Larmor frequency.

$$\omega_0 = \gamma B_0$$

of the observed nuclear spin by the amount $\gamma \sigma B_0$. For different proton species in a molecule (e.g. $CH_2$, $CH_3$, OH), the chemical shifts are in the range of 0-10 ppm, i.e., the Larmor frequency of the proton species observed is only shifted by the factor $10^{-6}$ to $10^{-5}$, multiplied by the Larmor frequency.

The chemical shift disappears when $B_0$ approaches zero. In small magnetic fields $B_0$, for example, in earth's magnetic field ($5 \cdot 10^{-5}$ T), the difference between the frequencies of two different proton species is therefore a few mHz. This small difference can not be observed, as a matter of principle, because the line widths of the $^1$H-NMR spectral lines are greater than 0.03 Hz. Thus, the larger and more homogenous the magnetic field $B_0$ is, the better the differences in chemical shift can be measured. This fact, and the signal-to-noise ratio, which becomes larger as the field increases, is the reason for the trend towards ever larger and more expensive superconducting magnets.

One exception from the rule that no chemical shifts can be measured in small magnetic field has become known, namely the high-resolution NMR spectroscopy of hyperpolarized Xe-atoms in earth's magnetic field "Appelt, S., Häsing, F. W., Kühn, H., Perlo, J. & Blümich, B. Mobile High Resolution Xenon Nuclear Magnetic Resonance Spectroscopy in the Earth's Magnetic Field. Phys. Rev. Lett. 94, 197602 (2005)". The reason for this exception is that the differences in chemical shift for Xe atoms is larger by two orders of magnitude than that of the protons, and that, at the same time, the line width of the Xe NMR-lines are extremely narrow (a few mHz).

Despite the chemical shift not being measurable for small magnetic fields in the case of most nuclei, in particular $<10^{-4}$ T, there has been a steady improvement of nuclear spin resonance measurements in small magnetic fields, hereinafter referred to as low-field NMR, in the past 50 years. Starting with the first $^1$H NMR spectrum in earth's magnetic field by Packard and Varian (see Kaplan, J. Minutes of the Stanford Meeting Dec. 28, 29, and 30, 1953. Phys. Rev. 93, 939-954 (1954); see page 941: Packard, M. & Varian, R. Free Nuclear Induction in the Earth's Magnetic Field), the development progressed to the measurement of the first heteronuclear $^1$H—$^{31}$P and $^1$H—$^{14}$N J-couplings [see Benoit, H., Hennequin, J. & Ottavi, H. Les applications spectroscopiques de la méthode de prépolarisation en R.M.N. (champs faibles). Chimie Analytique 44, 471-477 (1962); Béné, G. J. Nuclear Magnetism Of Liquid Systems In The Earth Field Range. Phys. Rep. 58, 213-267 (1980)], the measurement of self-diffusion of water [see Stepišnik, J., Kos, M., Planinšič, G. & Eržen, V. Strong Nonuniform Magnetic Field for Self-Diffusion Measurement by NMR in the Earth's Magnetic Field. J. Magn. Reson. Series A 107, 167-172 (1994)] in the pores of antarctic ice [see Callaghan, P. T., Eccles, C. D. & Seymour, J. D. An earth's field nuclear magnetic resonance apparatus suitable for pulsed gradient spin echo measurements of self-diffusion under Antarctic conditions. Rev. Sci. Instrum. 68, 4263-4270 (1997)], the detection of ground water reservoirs [see: Planinšič, G., Stepišnik, J. & Kos, M. Relaxation-Time Measurement and Imaging in the Earth's Magnetic Field. J. Magn. Reson. Series A 110, 170-174 (1994)], the magnetic resonance tomography in earth's magnetic field [see: Shushakov, A. Groundwater NMR in conductive water. Geophysics 61, 998-1006 (1996)], and finally the SQUID-detected NMR in the microtesla to nanotesla range [McDermott, R. et al. Liquid-State NMR and Scalar Couplings in Microtesla Magnetic Fields. Science 295, 2247-2249 (2002); Trabesinger, A. H. et al. SQUID-Detected Liquid State NMR in Microtesla Fields. J. Phys. Chem. A 108, 957-963 (2004); Burghoff, M., Hartwig, S., Trahms, L. & Bernarding, J. Nuclear magnetic resonance in the nanotesla range. Appl. Phys. Lett. 87, 054103 (2005); Greenberg, Y. S. Application of superconducting quantum interference devices to nuclear magnetic resonance. Rev. Mod. Phys. 70, 175-222 (1998); Clarke, J. in SQUID sensors: Fundamentals, Fabrication and Applications. Weinstock, H., Ed. (Kluwer Academic, Dordrecht, Nederlands, 1996), 1-62.].

Despite the small chemical shifts not being measurable, in the case of most nuclei, for small external magnetic fields of, for example, less than $10^{-4}$ T, information can nevertheless be obtained on the structure of molecules by exploiting the mechanism of J-coupling. J-coupling (also known as spin-spin coupling) between two nuclear spins [see: Proctor, W. G. & Yu, F. C. On the Nuclear Magnetic Moments of Several Stable Isotopes. Phys. Rev. 81, 20-30 (1951)] is caused by the indirect communication between a nuclear spin $I_A$ and a second nuclear spin $I_B$ conveyed through the electrons within the chemical bond between $I_a$ and $I_B$. The mathematical form of the interaction energy of the J-coupling $$H = 2\pi \cdot J \cdot I_A \cdot I_B$$

implies that the J-coupling energy (typically 0.1-200 Hz for protons) depends on their relative orientation of the two nuclear spins (parallel or antiparallel relative to the $B_0$ field), and that the J-coupling is independent from the external magnetic field $B_0$, which is very important indeed.

J-coupling between $I_a$ and $I_B$ may also occur across several chemical bonds. A rule of thumb states that, the larger the bond distance is (the more bonds are located between $I_A$ and $I_B$), the weaker the J-coupling constant or the J-coupling energy is. The independence of the J-coupling from the field $B_0$ means that the J-coupling constant can be measured with a high degree of accuracy, also in the case of arbitrarily small magnetic fields.

Quantum-mechanical calculations showed that a split in the NMR spectrum due to J-coupling is observable only if the difference of the Larmor frequencies of the nuclear spins $I_A$ and $I_B$ is larger than the J-coupling to be observed. A difference of the Larmor frequencies of $I_A$ and $I_B$ exists either because of their different chemical shifts or because of the different gyromagnetic ratios $\gamma_a$ und $\gamma_B$.

If the nuclei are different species with different gyromagnetic ratios $\gamma_A$ und $\gamma_B$ (e.g., $^1H$ and $^{19}F$), then the J-coupling is called heteronuclear. If $I_A$ and $I_B$ are of the same type (e.g., two protons), then the coupling is referred to as homonuclear. Therefore, the heteronuclear J-coupling is measurable down to very small magnetic fields (to ~$10^{-7}$ T), because the difference in Larmor frequencies of $I_A$ and $I_B$ is greater, even at $10^{-7}$ T, than the J-coupling.

The homonuclear J-coupling is another case. In earth's magnetic field, for example, the typical $^1H$-line width of ethanol is approximately 100 mHz, whereas the difference in the chemical shift of the protons of the $CH_2$ or the $CH_3$-group is a few mHz. Therefore, all protons of ethanol are magnetically equivalent in earth's magnetic field. The homonuclear J-coupling cannot be measured. This fact is shown for the ethanol molecule in FIG. 1. In the case of a high magnetic field—hereinafter referred to high-field—of about 1.5 T, the chemical shifts are much bigger than the $^1H$-line widths. Thus, the $^1H$-spectrum shows, on the one hand, the three chemical shifts of the OH, $CH_2$ and $CH_3$-groups, and on the other hand the homonuclear J-couplings of the $CH_2$-group (coupling with the protons of the $CH_3$-group: →quartet) and the $CH_3$-group (coupling with the protons of the $CH_2$-group: →triplet). The proton of the OH-group exhibits no homonuclear J-coupling with the other two groups because the proton can move freely because of the hydrogen bridge bond. In the high-field, the combination of the measured chemical shift with the homonuclear J-couplings permits an association with the structure of the ethanol molecule. This fact therefore forms the basis for the high-resolution high-field NMR.

Figure 1:
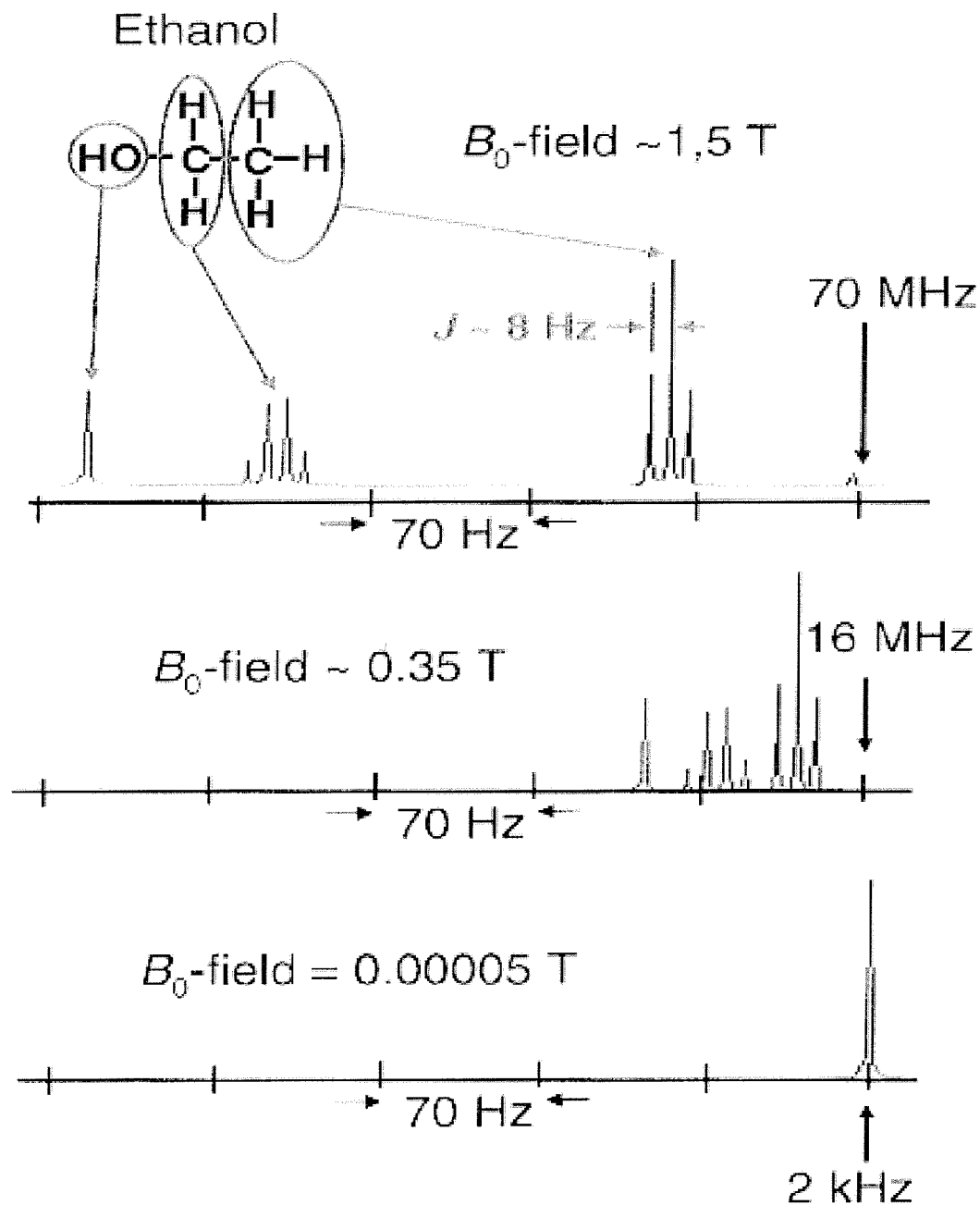
FIG. 1 shows the $^1H$-spectrum of ethanol.

The $B_0$-fields, which become smaller, move the OH, $CH_2$, and the $CH_3$-lines ever closer together, until they begin to merge, at a very low field. This collapse is demonstrated by way of example in FIG. 1 for three magnetic fields (1.5 T, 0.35 T, and in earth's magnetic field, $5 \cdot 10^{-5}$ T), with the entire ethanol spectrum, in earth's magnetic field, consisting of a single line without any structural information.

In recent years, ever more precise measurements of the heteronuclear J-couplings were successfully carried out for external magnetic fields smaller than $10^{-4}$ T. Some years ago, Mc Dermott et al. [see: McDermott, R. et al. Liquid-State NMR and Scalar Couplings in Microtesla Magnetic Fields. Science 295, 2247-2249 (2002)] demonstrated the measurement of the heteronuclear $^1H$—$^{31}P$ J-coupling constant with SQUID's in the nT range.

The $^1H$-line width, which in these experiments is dominated by the inhomogeneity of the $B_0$-field, is approximately 1 Hz. Only recently, the relevance of the ultra-high resolution $^1H$, $^{19}F$ und $^7Li$ NMR spectroscopy in earth's magnetic field was demonstrated by S. Appelt, H. Kühn, W. Häsing und B. Blümich in Nature Physics 2, 105-109 (2006), with $^1H$-line widths shown down to 0.03 Hz. The heteronuclear $^1H$—$^{19}F$ and $^1H$—$^{29}Si$ J-coupling constants of various molecules could be determined with an accuracy of a few mHz. This accuracy cannot be further improved upon because the measured line widths are already at the natural line width (given by the inverse of the transversal relaxation time $T_2$). What is most important, however, is that the accuracy of the measured J-coupling constants is better by one or two orders of magnitude, compared with the accuracy that can be achieved with superconducting high-field magnets. This extremely high resolution permits an exact classification or discrimination of chemical structures, both of small ones as well as of macromolecules. In future, this is going to have far-reaching consequences considering, for example, the technical realization of mobile low-field NMR devices for carrying out chemical analyses with a high degree of accuracy.

Figure 2:
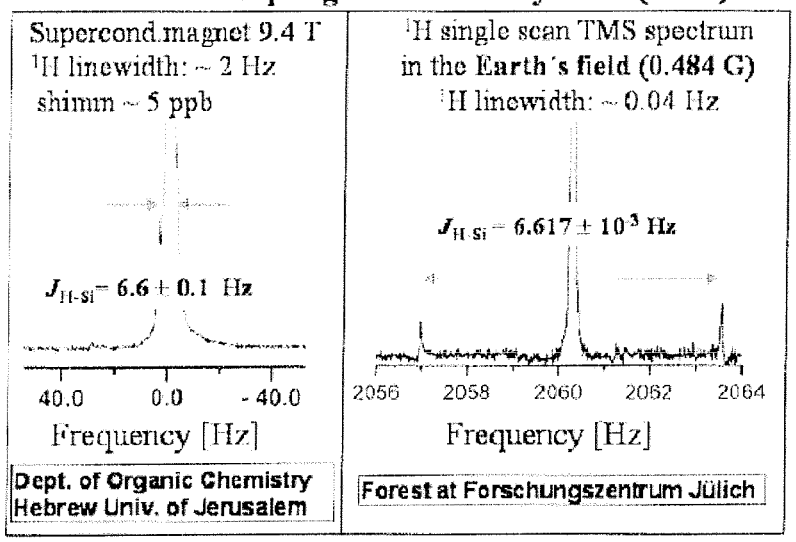
FIG. 2 shows the heteronuclear $^1H$—$^{29}Si$ J-coupling of TMS measured in a homogeneous (~3 ppb) 9.4 T high-field magnet and in Earth's magnetic field.

As an example for the high resolution of frequency in earth's magnetic field, FIG. 2 shows a comparison between the heteronuclear $^1H$—$^{29}Si$ J-coupling of tetramethyl silane (TMS) measured in a very homogeneous (~3 ppb) 9.4 T high-field magnet and the same J-coupling constant, but measured in earth's magnetic field. The $^1H$—$^{29}Si$ J-coupling in earth's magnetic field, at 6.617+1 mHz, is better by about two orders of magnitude than the J-coupling measured with the high-field magnet (J=6.6±0.1 Hz). (source: Nature Physics 2, 105-109 (2006)).

Figure 3:
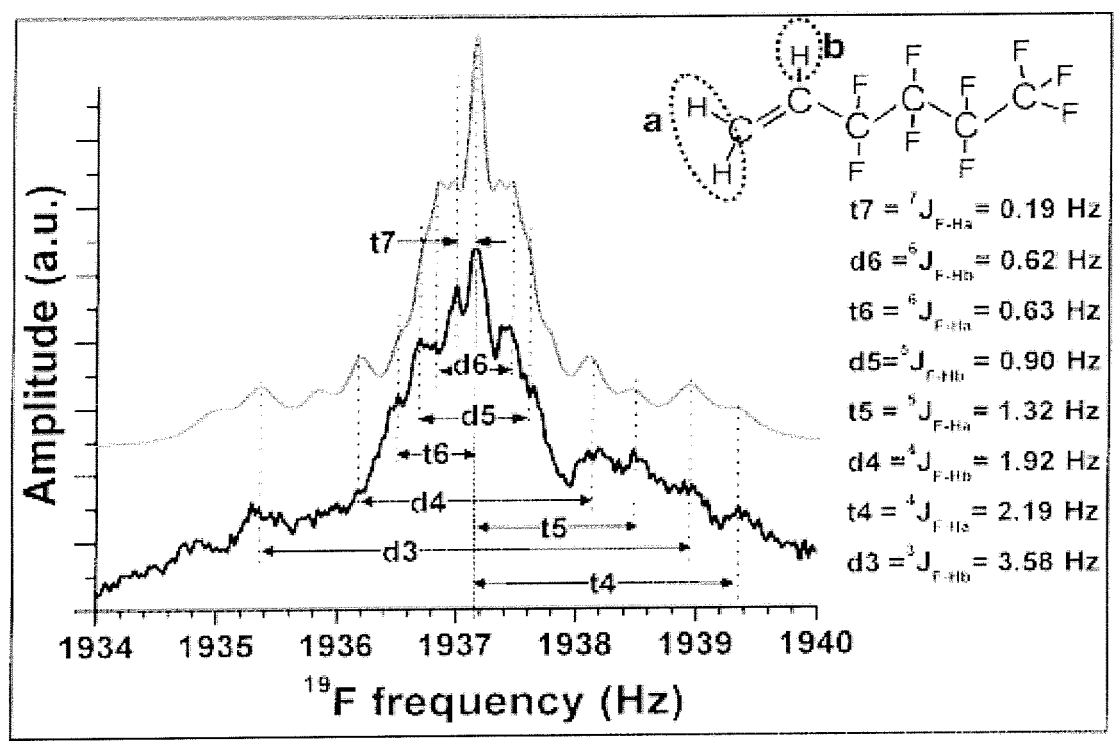
FIG. 3 is an Earth-field $^1H$ NMR spectrum of nonaflourohexene with eight heteronuclear $^1H$—$^{19}F$ J-couplings.

FIG. 3 shows another example for earth field NMR with the molecule nonafluorohexene with eight heteronuclear $^1$H—$^{19}$F J-couplings, which can all be identified in the spectrum. This is an example that demonstrates that the J-coupling network can be measured over a distance of many bonds in a single measurement, and that the molecular structure can thus be captured. The $^{19}$F-spectrum of nonafluorohexene (NFH) shown in FIG. 3 is characterized by eight heteronuclear $^1$H—$^{19}$F J-couplings. The $^{19}$F-spectrum consists of a superposition of 4 triplets and 4 doublets. The upper curve is a simulation of this superposition and shows that the molecule structure of NFH becomes visible with a single measurement. The number at the top left next to the J-coupling constant indicates the number of chemical bonds between the observed $^1$H and $^{19}$F nuclei. (source: Nature Physics 2, 105-109 (2006)).

According to the state of the art until now, the characterization of molecules by means of ultra-high resolution low-field NMR is, however, only possible with the help of heteronuclear J-couplings. Even though a high resolution of frequencies can successfully be achieved, the information obtained solely from the heteronuclear J-couplings do not, however, contain any information about the molecule groups occurring in a sample.

It is the object of the invention to be able to characterize a sample with a high resolution and comprehensively.

The object is solved by a method for examining a sample by means of nuclear magnetic spectroscopy by measuring homonuclear J-couplings in a small magnetic field and using the measured homonuclear couplings being used for characterizing the sample.

The person skilled in the art had the view that only heteronuclear J-couplings of a sample could be measured in small magnetic field (see for example Applied Physics Letters 87, 054103 (2005), Nuclear magnetic resonance in the nanotesla range, first page, left column, paragraph 2). However, the experts did not consider that practically all organic molecules or biomolecules consist mainly of carbon, hydrogen and oxygen, and that nuclei such as, for example, $^{19}$F or $^{29}$Si are relatively rare. Carbon consists of 99% $^{12}$C (with a nuclear spin I=0) and 1% $^{13}$C (with a nuclear spin I=½). 1% of all $^1$H nuclei of the organic molecule couple with a $^{13}$C nucleus in a heteronuclear manner. Thus, the 1H spectrum in the low-field consists mainly of a single $^1$H-line without structure (as is already suggested in FIG. 1 in earth's magnetic field) as well as very small satellite lines (approximately 200 times smaller than the main line) arising from the heteronuclear $^1$H—$^{13}$C J-couplings. Contrary to the experts' opinion, the structural determination is now possible at least for those $^1$H nuclei coupled in a heteronuclear way with $^{13}$C nuclei (1% occurrence) or other rare nuclei (e.g. $^{15}$N). This then leads to a measurable, high-resolution homonuclear J-coupled H-spectrum, which at the same time contains information about the heteronuclear couplings.

Contrary to the preconception prevailing among the experts, homonuclear J-couplings occurring in samples can, in principle, be indeed measured in small magnetic fields.

In order to be able to capture the spectrum of homonuclear J-couplings in practice, a pre-magnetization of the sample to be examined, for example in a strong magnetic field of preferably at least 1 Tesla, is carried out in one embodiment. In one embodiment, particularly strong magnets, preferably permanent magnets of one to two Tesla, are used for this purpose.

If measurements are to be conducted in small magnetic fields, the experts had, as a rule, used comparatively weak (electro-) magnets for pre-magnetization, with which magnetic fields of an order of magnitude of 0.1 to 0.3 Tesla were generated. In practice, such weak fields used for pre-magnetization result in measurement results that, as a rule, are unsatisfactory for carrying out the method claimed. Much stronger magnets are used for carrying out a pre-magnetization, thus departing from the path commonly used in the field.

In order to achieve a good frequency resolution, it is particularly significant to pay attention to a particularly good homogeneity of the weak magnetic field acting on the sample during the measurement. The sample volume is selected to be small in one embodiment in order to come close to this aim. In particular, a sample volume of less than 2 cm$^3$ is small within the sense of the invention. As a rule, the skilled person chose a sample with a volume of 500 cm$^3$ and more in measurements in weak magnetic fields. There is also a departure from the measures common in the field in this respect.

In one embodiment, the samples are enriched suitably, for example with $^{13}$C nuclei in order to ensure in an improved manner that the method can be carried out. The measured results are subsequently used for a chemical characterization. Thus, the ability is successfully attained of measuring with a considerably greater accuracy and thus characterizing a sample, i.e. primarily an organic sample, with considerably greater accuracy, and in earth's magnetic field. As a rule, however, the method according to the invention can also be carried out without such an enrichment. Characterization in earth's magnetic field simplifies characterization because earth's magnetic field is at one's disposal as a matter of course, without having to resort to a technical effort.

Figure 4:
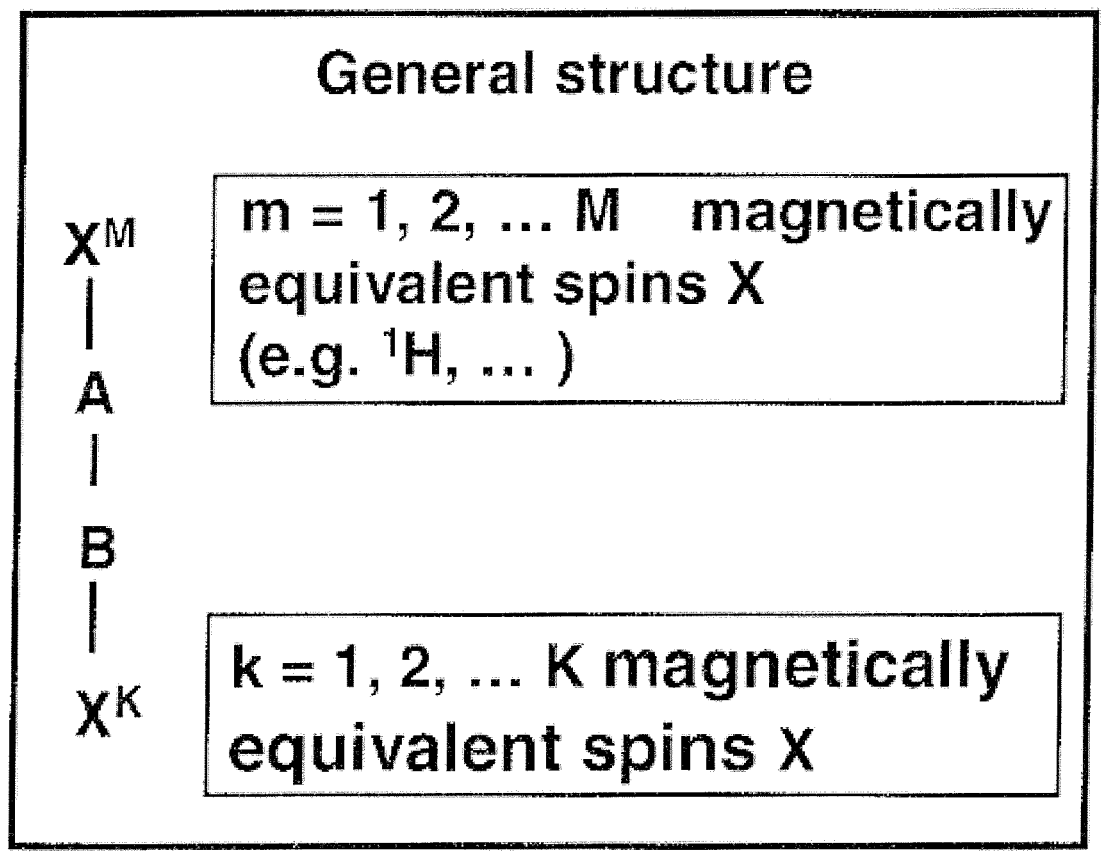
FIG. 4 illustrates a generic molecular skeleton $X^M$-A-B—$X^K$.

As FIG. 4 illustrates, a sample, for instance, consists of molecules having the skeleton $X^M$-A-B—$X^K$. A and B are arbitrary molecular groups to which the magnetically equivalent spins X are bonded. m=1, 2, . . . , M spins of the type X, hereinafter referred to as $X^M$, are bonded to the molecular group A. k=1, 2, . . . , K spins of the type X, hereinafter referred to as $X^K$, are bonded to the molecular group B. X represents, e.g., the proton or another nucleus to be measured. Such a molecule, for example, comprises $^{13}$C atoms with a natural occurrence of 1%, for example in the part A of the molecule.

Let, for example, M=3 and K=2. The two $^1$H—$^{13}$C heteronuclear coupling constant of $X^M$ with $^{13}$C and $X^K$ with $^{13}$C are then designated $J_{H-A}$ and $J_{H—B-A}$ and the $^1$H homonuclear coupling constant between $X^M$ and $X^K$ is designated $J_{H-H}$. Because the bond distance between $X^M$ and A is smaller than between $X^K$ and A, $J_{H-A}>J_{H—B-A}>J_{H-H}$ applies as a matter of principle. Then, an H-NMR spectrum is regularly measured in the low-field, the spectrum at first typically comprising a large central line caused by all magnetically equivalent and uncoupled spins $X^M$ and $X^K$. In addition, the spectrum comprises two symmetrical multiplet structures whose intensities are approximately 1000 times lower, compared with the intensity of the central line. The two multiplet structures typically consist of two quartets and two triplets whose splitting patterns are caused by the homonuclear J-coupling between $X^3$ and $X^2$. The four lines of the quartet structure with intensity ratios of typically 1:3:3:1 and the distance $J_{H-H}$ in the frequency space belong to the NMR signal of the two protons of the $X^2$-group, which couple in a homonuclear fashion to the 8 possible configurations of the three protons of the $X^3$-group. Conversely, the three lines of the triplet structure with the typical intensity ratios 1:2:1 and the same distance $J_{H-H}$ belong to the NMR signal of the three protons of the $X^3$-group that couple to the 4 possible configurations of the two protons of the $X^2$-group in a homonuclear manner. That the quartet (or triplet structure) typically splits symmetrically in two identical sub-groups around the central line is caused by the heteronuclear $^1H$—$^{13}C$ J-coupling $J_{H-B-A}$ (or $J_{H-A}$). In this case, the $^{13}C$ nuclear spin can either be parallel or antiparallel relative to the field B0, and shifts the quartet structure (triplet structure) away from the central line by $\pm J_{H-B-A}/2$ ($\pm J_{H-A}/2$). This measurable spectrum is shown in FIG. 3.

A homonuclear J-coupling between the $X^M$ and the $X^K$ spins in the low-field is, in any case, measurable if the following equation is met.

$$|J_{X^m\text{-}A}-J_{X^k\text{-}B\text{-}A}|>|J_{X^mX^k}|$$

In this case, $J_{X_mX_k}$ is defined as the homonuclear J-coupling constant between the nucleus $X^m$ (m=[1, . . . M]) and the nucleus $X^k$ (k=[1, . . . K]). In a natural sample, as a rule, there is at least one heteronucleus unequal to X in a sufficient concentration in the part A of the molecule, and the two heteronuclear J-coupling constant $J_{X-A}$ and $J_{X-B-A}$ are different as regards their amount. If the equation is met, then the magnetic equivalence between the $X^m$ and the $X^k$ nucleus is cancelled because the couplings $J_{X-A} \neq J_{X-B-A}$ cause unequal splits of the NMR spectral lines of the X nuclei and thus shift the originally equal transition frequencies of $X^m$ and $X^k$ in a different extent. The nucleus $X^m$ can then make a magnetic transition, independent from the orientation of the spin of the nucleus $X^k$, when its transition frequency (given by $\omega_H+J_{Xm}/2$) is sufficiently distant from the transition frequency of the nucleus $X^k$ (given by $\omega_H+J_{Xk}/2$). This difference in frequency between the nuclei $X^m$ and $X^k$ must be larger than the homonuclear J-coupling between $X^m$ and $X^k$, because the other nucleus $X^k$ is otherwise "swept along" during the magnetic transition of one nucleus $X^m$, and thus the homonuclear J-coupling cannot be measured anymore, as a matter of principle. In practice, real samples meet these required boundary conditions as a matter of principle, so that various samples can be characterized successfully by the method according to the invention.

In one embodiment, organic molecules are used as a sample, because organic samples in most cases meet the requirements for being able to carry out the method. The method is used primarily, when a sample consisting of organic molecules is to be located or characterized.

In order to ensure a further improved operational capability of the method, the sample is selected such that at least two different heteronuclear J-couplings that meet the equation $$|J_{X^m\text{-}A}-J_{X^k\text{-}B\text{-}A}|>|J_{X^mX^k}|$$

are present in a molecule. As a rule, that is the case in organic samples. The method is applied in particular if such a sample is to be located. Otherwise, the sample is enriched suitably prior to the method being carried out.

A small exterior magnetic field $B_0$ within the sense of the invention is present particularly, if it is smaller than $10^{-4}$ T. Earth's magnetic field is preferably used as a small external magnetic field, because it is basically particularly homogeneous. A particularly homogeneous external magnetic field is advantageous for obtaining good measurement results.

In order to have a further improved capability for characterization, heteronuclear J-couplings of the sample are measured additionally and used for characterization. On the whole, a sample can thus be characterized completely and in a significantly improved manner compared with the state of the art.

In order to be able to measure in a manner improved further, the sample is pre-magnetized by hyperpolarization of the nuclear spin in one embodiment. The signal-to-noise ratio is thus enhanced.

Despite the absence of chemical shift information, a detailed structural determination is possible by means of the method. The skilled person held the view that he would have to know the chemical shift information as well as the heteronuclear J-couplings for a detailed molecular structural determination. In the method according to the invention, this knowledge is not necessary, because homonuclear J-couplings are observed and because they, together with heteronuclear J-couplings, enable a detailed molecular structural determination in an even more improved manner.

On the one hand, the spectra can be interpreted. On the other hand, a sample can be analyzed by comparing the spectrum with known spectra. If a spectrum that is already known is found in the sample, this implies that the sample has the substance of the known spectrum.

The invention is explained further below by means of figures and embodiments.

Figure 5:
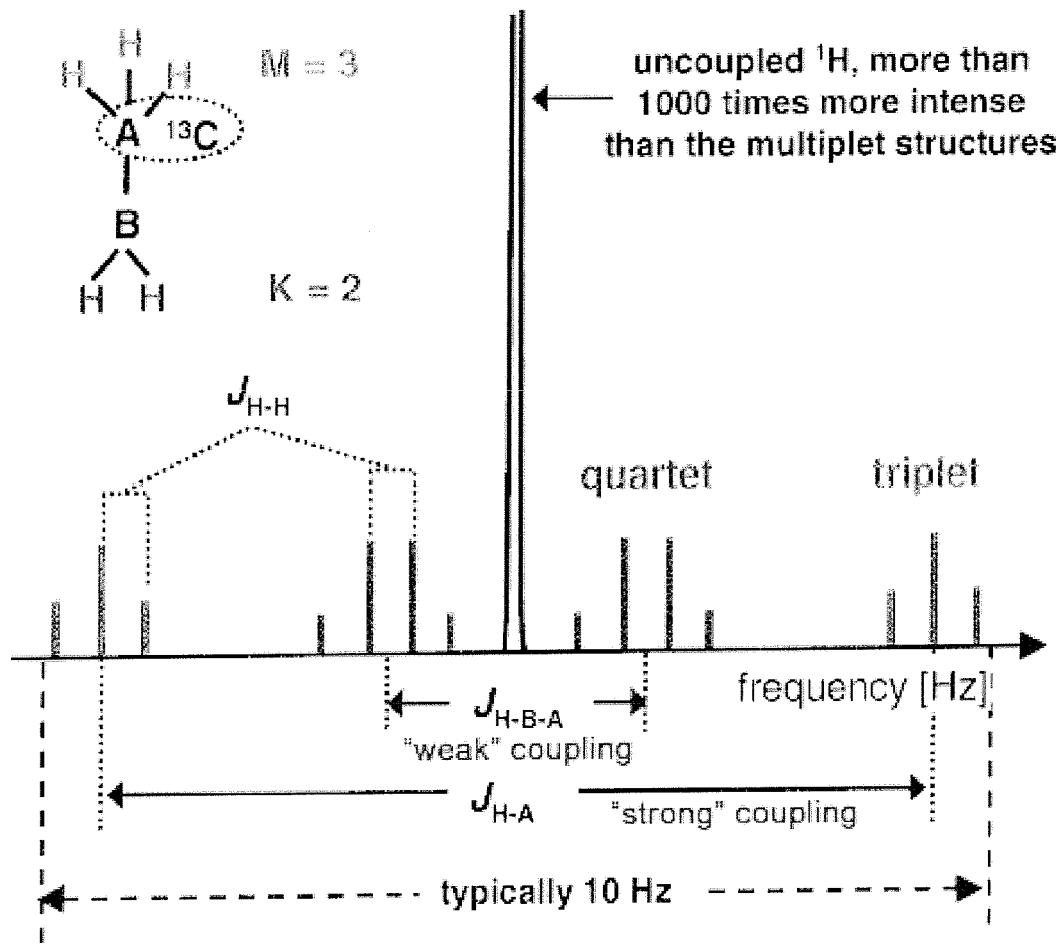
FIG. 5 shows the structure of the homonuclear-coupled spectrum in the low-field for the molecule $H^3$—C—B—$H^2$ for the case of the weak coupling limit.

FIG. 5 shows the structure of the homonuclear-coupled spectrum in the low-field for the molecule $X^M$-A-B—$X^K$, namely for a molecule having the structure $H^3$—C—B—$H^2$ for the case of the weak coupling limit ($|\omega_H-\omega_C|>>|J_{H-C}|$). The $^{13}C$ nucleus has an occurrence of 1% in the group A. This structure of the spectrum looks totally different in the low-field than in the high-field. For the case where X denotes protons ($^1H$), FIG. 5 furthermore shows M=3, K=2, and that, for 1% of all molecules $X^M$-A-B—$X^K$, there is an $^{13}C$ nucleus in the group A with I=½ (natural occurrence of $^{13}C$=1%). The two $^1H$—$^{13}C$ heteronuclear coupling constants of $X^M$ with $^{13}C$ and $X^K$ with $^{13}C$ are designated $J_{H-A}$ and $J_{H-B-A}$, and the $^1H$ homonuclear coupling constant between $X^M$ and $X^K$ with $J_{H-H}$ $\omega_H$ ($\omega_C$) means the Larmor frequency for the $^1H$ ($^{13}C$) nuclei. Since the bond distance between $X^M$ and A is smaller than between $X^K$ and A, the following applies $$|J_{H\text{-}C}-J_{H\text{-}B\text{-}C}|>|J_{HH}|.$$

The $^1H$-NMR spectrum in the low-field for the case of the weak coupling limit ($\omega_H-\omega_C>>J_{H-A}$) shown in FIG. 5 on the one hand consists of a large central line arising from all magnetically equivalent and uncoupled spins $X^M$ and $X^K$, and on the other hand, from two symmetrical multiplet structures whose intensities are 1000 times lower compared to the intensities of the central line. The two multiplet structures consist of two quartets and two triplets whose splitting patterns are caused by the homonuclear J-coupling between $X^3$ and $X^2$ The four lines of the quartet structure with intensity ratios of 1:3:3:1 and the distance $J_{H-H}$ in the frequency space belong to the NMR signal of the two protons of the $X^2$-group, which couple in a homonuclear fashion to the 8 possible configurations of the three protons of the $X^3$-group. Conversely, the three lines of the triplet structure with the intensity ratios 1:2:1 and the same distance $J_{H-H}$ belong to the NMR signal of the three protons of the $X^3$-group that couple to the 4 possible configurations of the two protons of the $X^2$-group in a homonuclear manner. That the t (or triplet structure) split up symmetrically around the central line into two identical sub-groups is caused by the heteronuclear $^1H$—$^{13}C$ J-coupling $J_{H-B-A}$ (or $J_{H-A}$). In this case, the $^{13}C$ nuclear spin can either be parallel or antiparallel relative to the field $B_0$, and shifts the quartet structure (triplet structure) away from the central line by $\pm J_{H-B-A}/2$ ($\pm J_{H-A}/2$).

Figure 6:
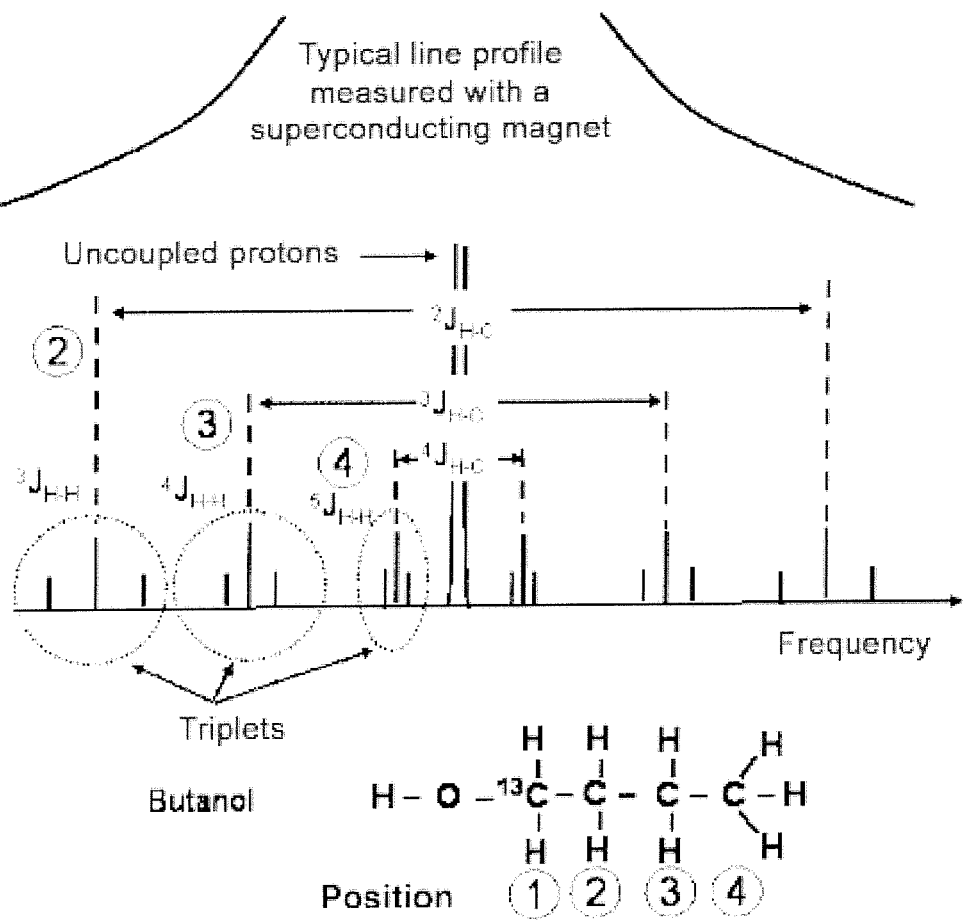
FIG. 6 is a schematic of all homonuclear $^1H$—$^1H$ J-couplings that are observable in the low-field for n-butanol in the case of the weak coupling limit.

FIG. 6 shows schematically all homonuclear $^1$H—$^1$H J-couplings that are observable in the low-field for the more complicated case of the n-butanol in the case of the weak coupling limit.

The n-butanol molecule consists of 4 carbon atoms in linear arrangement with four possible positions (1-4 in FIG. 6) for the $^{13}$C nuclear spin. If the $^{13}$C nuclear spin is located at position 1 of the butanol, the protons of the CH$_2$ groups couple to the positions 2 and 3, or of the CH$_3$ group to the position 4, in a homonuclear fashion to the two protons of the CH$_2$ group at position 1. Triplet pairs with the frequency distances $^2J_{H-C}$, $^3J_{H-C}$ and $^4J_{H-C}$ arranged symmetrically around the main line result therefrom. The number at the top left next to the J-coupling constant indicates the number of chemical bonds between the observed nuclei. The individual triplets in turn reflect the homonuclear $^1$H—$^1$H J-couplings of the CH$_2$ or the CH$_3$ groups (position 2-4) with the protons of the CH$_2$ groups at position 1. Because of the different bond distances three different homonuclear coupling constants $^3J_{H-HC}$>$^4J_{H-H}$>$^5J_{H-H}$ exist. The plurality of J-coupled lines permits a structural identification of the molecule at hand.

If the $^{13}$C spin is located at position 2 or 3, then a similar coupling pattern constituted of three triplet pairs is the result, however, the J-coupling constants may all be different from the ones shown before. If the $^{13}$C spin is located at position 4, accordingly, three quartet pairs, also with different homonuclear and heteronuclear J-coupling constants, are the result. The J-coupling pattern in its entirety is characteristic for the n-butanol molecule. In this manner, a fingerprint of the structure of the n-butanol molecule is obtained, or the fingerprint can be measured according to the invention, in the low-field with the measurement of the heteronuclear and homonuclear network and without knowledge of the chemical shifts. It can be said, generally, that the method according to the invention can also be applied to complex molecules and without complicated high frequency electronic systems, superconducting magnets or elaborate cooling technologies (SQUIDs).

If the condition of the weak coupling limit is not met, then the spectrum is more complicated. If, as for example in FIG. 5, a strongly coupled CH$_3$ group ($\omega_H$−$\omega_C$~$J_{H-C}$) is concerned, then the quartet pair becomes an octet pair, and the triplet pair becomes a pair of 9 lines.

Because the homonuclear J-coupling constant between the $X^M$ and the $X^K$ nuclei can be very small (as a rule, <1 Hz), the spectrometer used ought to operate with the best possible frequency resolution. Ideally, the spectrometer should exhibit a negligible instrumental line broadening, i.e., the widths of the spectral lines are close to the (smallest possible) natural line width.

For the same reasons, attention should be paid to the low-field NMR spectrometer used being very sensitive. The signal-to-noise ratio should be far more than 1000 for the main line, so that the few X nuclei that are coupled in a heteronuclear manner to the rare nuclei (e.g. $^{13}$C at 1% occurrence) can be observed reliably. If the rare nuclei are, for example $^{15}$N (I=½), then the requirements concerning the sensitivity of the spectrometer are even higher, because the natural occurrence of the $^{15}$N nuclei is 0.36%.

If the sensitivity of the NMR spectrometer used is not sufficient, the sample to be examined may be enriched with isotopes, that is, for example, with $^{13}$C. Then, the intensity of all homonuclear $^1$H—$^1$H coupled lines increases by up to two orders of magnitude. This means that the requirements for the sensitivity of the spectrometer are not as high anymore. However, enrichment is a very expensive method and can hardly be carried out in mobile applications (for example, the online analysis of the molecules of petroleum).

Figure 7:
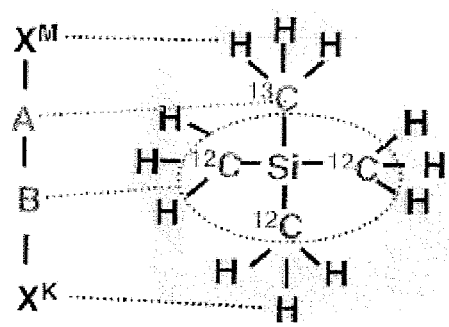
FIG. 7 shows the structure of TMS determined according to the allocation of the molecular fragments with the general configuration $X^M$-A-B—$X^K$, where $X=^1H$, $M=3$, $K=9$, $A=^{13}C$ and $B=(^{12}C)_3$—Si.

FIG. 7 shows the structure of the molecule tetramethyl silane (TMS) determined according to the method and the allocation of the molecular fragments of the TMS to the general configuration of a molecule $X^M$-A-B—$X^K$. For this example, X—$^1$H, M=3, K=9, A=$^{13}$C and B—($^{12}$C)$_3$—Si.

For about 1% of all TMS molecules, a $^{12}$C nucleus with a spin I=0 is replaced by a $^{13}$C nucleus with a spin I=1/2. Therefore, the A group here simply is a $^{13}$C nucleus, the B group consists of three $^{12}$C atoms bonded to a central Si atom. In nature, silicon consists of 95% $^{28}$Si with nuclear spin I=0 and of 4.7% Si with nuclear spin I=½. The X nuclei to be measured are protons, with M=3 magnetically equivalent protons bonded to the group A (=$^{13}$C) and K=9 magnetically equivalent protons bonded to the Group B. Because 4.7% of all Si atoms are $^{29}$Si atoms with a nuclear spin I=½, a splitting of the $^1$H spectrum into two lines takes place due to the heteronuclear coupling with $J_{H—Si}$=6.617 Hz between the 12 protons and the $^{29}$Si. This J-coupled duplet ($^{29}$Si nucleus is parallel or antiparallel relative to the field $B_0$) was already illustrated in FIG. 2.

Figure 8:
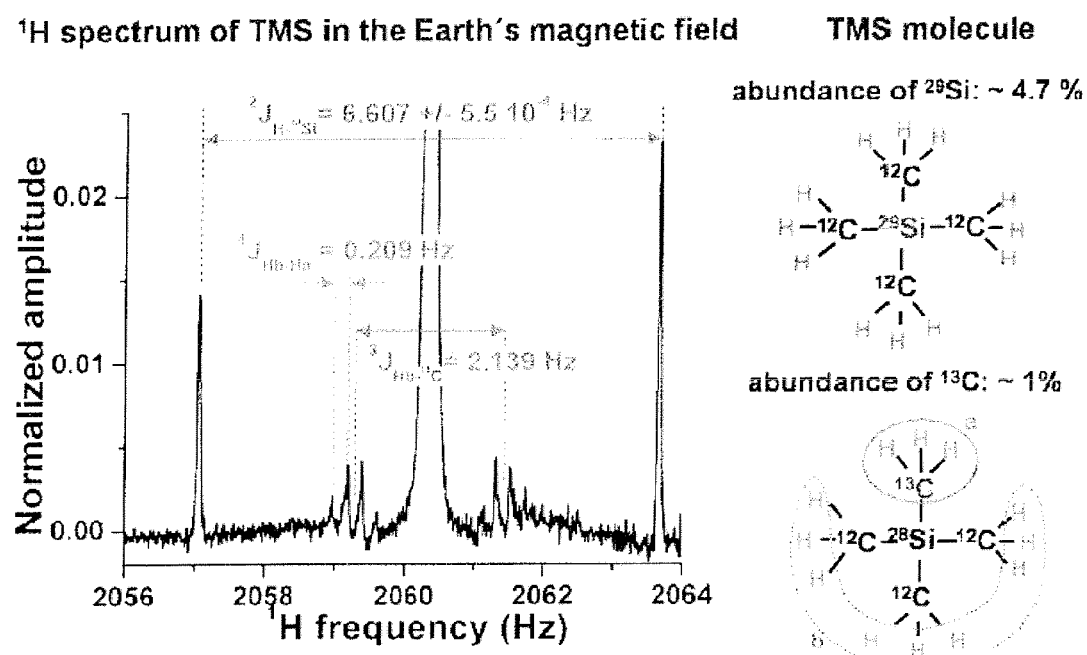
FIG. 8 is a $^1H$-NMR spectrum of TMS in Earth's magnetic field.

There is now, in a single one of one hundred TMS molecules, a $^{13}$C nucleus (1% occurrence) in the A group, and this cancels, through the two different heteronuclear $^1$H—$^{13}$C couplings ($^1J_{H-A}$~120 Hz und $^3J_{H-B-A}$~2 Hz) the magnetic equivalence of the 12 protons. The K=9 magnetically equivalent protons on the B group now couple in a homonuclear manner to the M=3 magnetically equivalent protons at the A group with the homonuclear coupling constants $^4J_{H-H}$<<1 Hz. Since the M=3 protons have 8 possible configurations (all three $^1$H up, or all three $^1$H down, or two up and one down, or one up and two down, with one threefold degeneracy each), two quartet structures having the frequency distance 3./h-b-a~2 Hz are measured, as FIG. 8 illustrates. What is shown is the measurement of a homonuclear $^1$H—$^1$H coupling of TMS in earth's magnetic field by means of $^1$H-NMR. At the same time, the heteronuclear $^1$H—$^{29}$Si (with $J_{H—Si}$=6.617 Hz), the $^1$H—$^{13}$C J-coupling (with $^3J_{H-B-A}$=2.139 Hz) and the homonuclear $^1$H—$^1$H coupling with the quartet pair with $^4J_{H-H}$=0.209 Hz is observed with a high resolution. Extremely small homonuclear J-couplings (0.209 Hz) can thus be measured with utmost precision and thus, minute structural differences of the molecule can be captured. Thus, the entire molecular structure is captured in a single spectrum.

The potential of the proposed method for structural elucidation is even greater if X=$^{13}$C is used as the nucleus to be measured. Compared to the proton spectra, the spectral resolution is better by more than a factor of 10, because the $T_2$ relaxation times for the $^{13}$C nuclei can become very long ($T_2$~3 s to 3 min). Because of a very small signal-to-noise ratio, however, a powerful pre-magnetization must be employed, such as for example the PHIP (Para Hydrogen Induced Polarization Transfer), SEOP (Spin Exchange Optical Pumping) or SPINOE (Spin Polarized Induced Nuclear Overhauser Effect) methods [see: Bowers, C. R. & Weitekamp, D. P. Transformation of symmetrization order to nuclear-spin magnetization by chemical reaction and nuclear magnetic resonance. Phys. Rev. Lett. 57, 2645-2648 (1986); Goldman, M., Jóhannesson, H., Axelsson, O. & Karlsson, M. Hyperpolarization of $^{13}$C through order transfer from parahydrogen: A new contrast agent for MRI. Magn. Reson. Imag. 23, 153-157 (2005); Happer, W. Optical Pumping. Rev. Mod. Phys. 44, 169-249 (1972); Appelt, S. et al. Theory of Spin-Exchange Optical Pumping of $^3$He and $^{129}$Xe, Phys. Rev. A 58, 1412-1439 (1998); Bouchiat, M. A., Carver, T. R. & Varnum, C. M. Nuclear Polarization in He$^3$ Gas Induced by Optical Pumping and Dipolar Exchange. Phys. Rev. Lett. 5, 373-375 (1960); Colegrove, F. D., Schearer, L. D. & Walters, G. K. Polarization of He³ Gas by Optical Pumping. Phys. Rev. 132, 2561-2572 (1963)].

Only the one-dimensional case of the NMR spectroscopy for fields <$10^{-4}$ T was treated until now. In the NMR spectra with the different multiplet pairs, it is possible to deduce unequivocally the number of the measured nuclei (e.g. $^1$H, $^{13}$C, ...) bonded to the A or B group. Even though all heteronuclear coupling constants can be determined from the spectrum, it is not possible in every case to deduce with which nucleus the measured nuclei couple. This problem is solved by introducing a second dimension in the frequency space into the spectrum. In a similar way as in the two-dimensional NMR [see: Ernst, R. R., Bodenhausen, G. & Wokaun, A. Principles of Nuclear Magnetic Resonance in One and Two Dimensions (Clarendon Press, Oxford, UK, 1987)], it is possible to, for example radiate continuously with a radio frequency with low intensity during the measurement of the spectrum. The radiated frequency should be distant enough from the Larmor frequency of the measured nuclei so as not to disturb the measurement of the signal of the measured nuclei. If the radio frequency is in resonance with the unknown nucleus which engages in a heteronuclear coupling with the measured nuclei, then the heteronuclear J-coupling averages out and the corresponding multiplet pair disappears in the spectrum. Because the frequency of the radiation is known, it is possible to conclude which type of nucleus it is. If the one-dimensional experiment with the measured nucleus is repeated at many different radio frequencies, a two-dimensional NMR spectrum is obtained, with all heteronuclear and homonuclear J-couplings of the measured nuclei being spanned in the frequency space in the first dimension, and with all types of nucleus (except for the protons) that are coupled with the measured nuclei in a heteronuclear manner being spanned in the frequency space in the second dimension.

Figure 9:
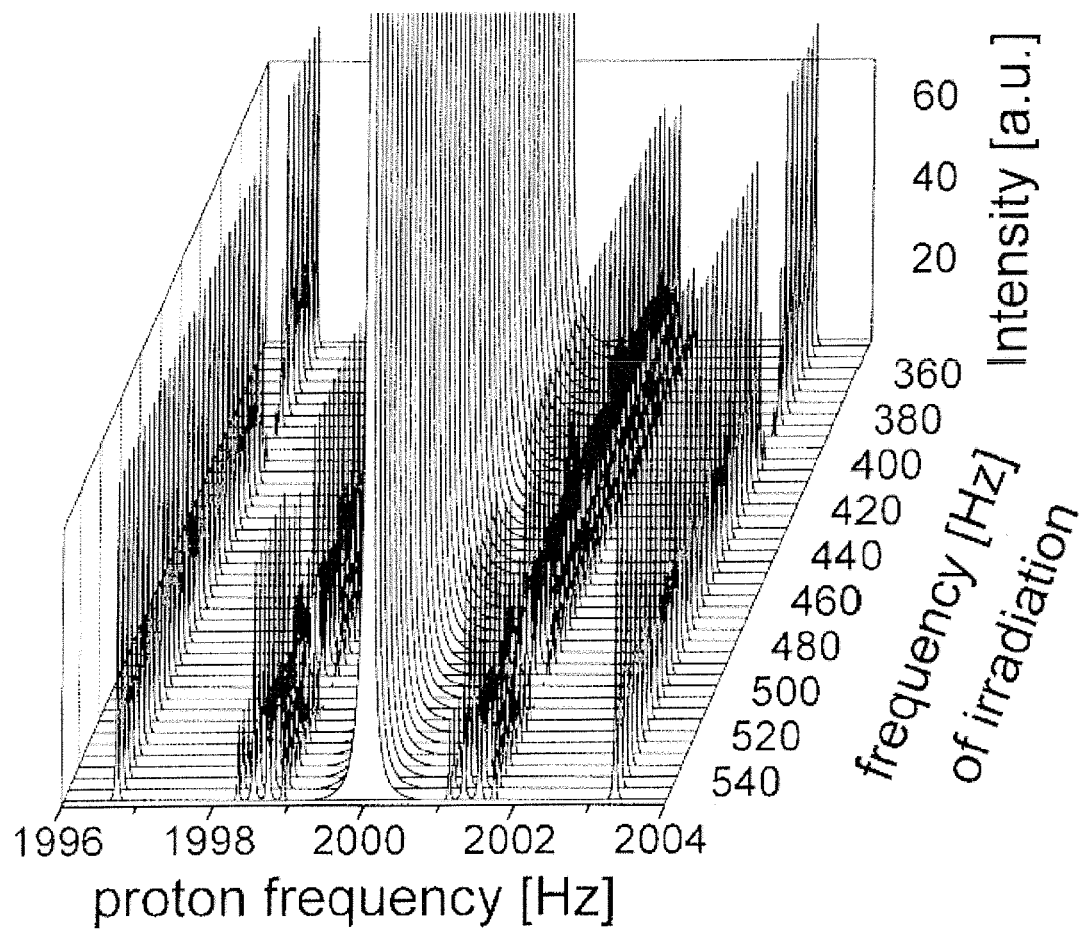
FIG. 9 is a simulated $^1H$ 2D spectrum of TMS in Earth's magnetic field.

In the case of the TMS molecule in earth's magnetic field ($4.698 \cdot 10^{-5}$ T) with the corresponding Larmor frequency of the protons ($\gamma_H$=4.257 kHz/G) at 2000 Hz. The Larmor frequency of $^{13}$C, then, is 503 Hz ($\gamma_{13C}$=1.0708 kHz/G) and that of $^{29}$Si is at 397.7 Hz ($\gamma_{29Si}$=-0.8465 kHz/G). If one now radiates, for example, at exactly 503 Hz with the field strength $B_1$, then the $^{13}$C magnetization oscillates at the Rabi frequency $V_R=\gamma_{13C} B_1$ and averages out the heteronuclear $^1$H—$^{13}$C J-coupling. In the one-dimensional $^1$H TMS spectrum, the quartet pair shown in FIG. 8 then disappears, because the condition for the appearance of the quartet pair is the existence of the heteronuclear $^1$H—$^{13}$C coupling. In the same way, the heteronuclear $^1$H—$^{29}$Si J-coupling averages out if radiation of 397.7 Hz is used. Thus, dips of the multiplet structure appear on the proton 2D spectrum exactly in those places where the heteronuclei are in resonance. This is illustrated in FIG. 9, where a simulated $^1$H 2D spectrum in earth's magnetic field is shown for the TMS molecule. An even better mapping of the molecular structure, compared with the 1D spectrum, is possible, because, apart from all J-coupling constants, all types of nucleus involved, including their associated J-couplings, are now known from the 2D spectrum.

The proposed 2D low-field NMR method can be improved upon even further, if, in one embodiment, a larger magnetic field in the mT range is selected instead of earth's magnetic field. At 1 mT (=$10^{-3}$ T), the Larmor frequency of the $^{13}$C nuclei is approximately 10 kHz. Because the range of the $^{13}$C chemical shifts is about 100 ppm, the differences of the $^{13}$C resonance frequencies due to different chemical environments are at about 1 Hz. Provided that the magnetic field $B_0$=1 mT is very homogeneous ($\Delta B_0/B_0 \sim 10^{-6}$) and temporally stable, then it is possible, in the $^1$H 2D spectrum (42 kHz Larmor frequency) to distinguish between the various $^{13}$C chemical shifts by varying the radiated $^{13}$C radio frequency (for example in 10 mHz steps). In the 2D spectrum, this permits an allocation of every measured $^{13}$C chemical shift with the associated J-multiplet pair and thus allows for a final elucidation of the molecular structure.

With the methods hitherto described, the mobile structural elucidation of petroleum molecules, for example, is possible. Due to the homonuclear and heteronuclear J-couplings, it is possible to distinguish, for example, between heptane, octane, benzole and other petroleum components on-site during the petroleum exploration (already at or in the well) and thus to classify the quality of the petroleum in a most precise manner.

Chemical reactions that take place, for example, in a technical process under difficult conditions (e.g. in larger reaction chambers) could be characterized by means of the (mobile) NMR according to the method, during the progress of the reaction. This is important, for example, for the online characterization of polymerization reactions during the production of plastics.

The quality assurance of liquid foodstuff products (e.g. alcoholic beverages, ethanol, water aromatic compound content, etc.) is another area of application for the method.

Finally, mobile NMR devices that map the structure of small to medium-sized proteins or biomolecules are of great interest in the pharmaceutical industry. The proposed method enables the use of mobile NMR devices that are substantially more flexible and cheaper in comparison to the performance of structural analyses with superconducting magnets.

An apparatus for carrying out the method for mobile high-resolution NMR is described below.

Figure 10:
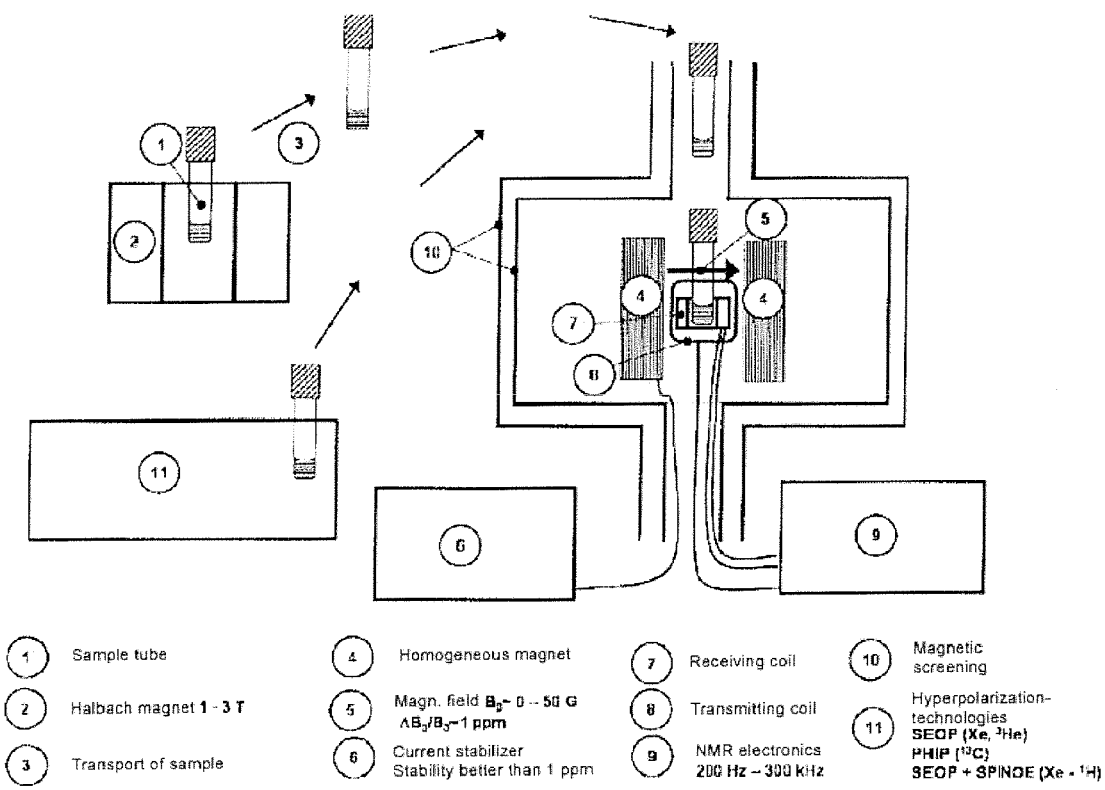
FIG. 10 is a schematic of an ultra-high resolution NMR spectroscope.

The central unit of the apparatus shown in FIG. 10 consists of two Helmholtz coils (4) that generates as homogeneous a magnetic field (5) ($B_0$=0.2-200 G) as possible. In this case, the homogeneity $\Delta B/B_0$ must at least be 1 ppm. In order to achieve a sufficient temporal stability of the $B_0$ field, the current stabilizer (6) must have a temporal stability of better than 1 ppm over 1 h. If necessary, the homogeneity must be obtained by using additional shim coils. The screening (10) serves the purpose of avoiding changes or distortions of the magnetic field due to environment at the measurement location.

The desired polarization of the sample (1) to be measured is achieved either by a pre-magnetization in a Halbach magnet (2) or by means of other hyperpolarization technologies (11) (SEOP, PHIP, SEOP+SPINOE) with subsequent transport (5) of the sample into the measurement coil (7). In the case of samples with short longitudinal relaxation times ($T_1$<1 s), the transport from the Halbach magnet (2) to the measurement coil (7) can be effected in about 100 ms by means of compressed air.

The sample is excited by the transmitter coil (8) with a DC or AC pulse generated by the NMR electronic system (9). Then, the "free induction decay" (FID) is measured with the receiver coil (7) and the NMR electronic system (9), and recorded by means of a data acquisition system and then evaluated.

The arrangement shown in FIG. 10 makes a mobile performance of ultra-high resolution NMR spectroscopy possible. A magnetic double screening with a screening factor of at least 5000 as well as a highly sensitive NMR electronic system having a signal-to-noise ratio of several thousand in relation to the uncoupled protons are special features.

Let us once more discuss the principle of the measurement of homo-nuclear J-couplings in ultra-low fields. Consider a simple molecule consisting of two chemical groups A and B without nuclear spin and with protons $^1$H attached to each (FIG. 11a, left). There are two different chemical shifts with transition frequencies $\omega_{H,A}$ and $\omega_{H,B}$ for $^1$H-A and B—$^1$H, respectively, and a homo-nuclear J-coupling constant $J^{hom}$. The coupling constant can readily be measured in the weak coupling limit $|\omega_{H,A}-\omega_{H,B}|>>2\pi|J^{hom}|$ which is nearly always fulfilled at high field. But at ultra-low fields with a magnetic field strength $B_0<10^{-4}$ T, the strong coupling limit applies with $|\omega_{H,A}-\omega_{H,B}|<<2\pi|J^{hom}|$. The two limits are illustrated by a mechanical analogon from two coupled oscillators in FIG. 1a, right. Each oscillator represents one chemical group i where i=H-A, H—B of the $^1$H-A-B—$^1$H molecule and consists of a spring with spring constant $D_i$ and mass m. The two oscillation frequencies are $\omega_i=(D_i/m)^{1/2}$. In this model, the homo-nuclear J-coupling between the two protons corresponds to the spring with constant $D^{hom}$ between the two masses. At high field, the two groups are magnetically inequivalent, $|\omega_{H,A}-\omega_{H,B}|>>(D^{hom}/m)^{1/2}$, so that $\omega_{H,A}\neq\omega_{H,B}$, and the spring introduces a beat with a frequency $(D^{hom}/m)^{1/2}$. The stick spectrum (FIG. 11b) shows the chemical shifts of the two frequencies and the splitting of the shifted $^1$H lines by the homo-nuclear J-coupling. At ultra-low field, the two groups are magnetically equivalent as the two spring constants are identical ($D_{H,A}=D_{H,B}$). The two masses will oscillate in phase with following identical displacements, and the spring constant $D^{hom}$ does not affect the motion. Therefore the spectrum consists only of one line at the frequency $\omega_H=\omega_{H,A}=\omega_{H,B}$ (FIG. 11c). In this case no information about the homo-nuclear J-coupling constant is available.

In FIG. 11d, the spring model is extended by two additional springs with constants $D_{H,C}^{het}\neq D_{H,B,C}^{het}$ in parallel to the springs with $D_{H,C}$ and $D_{H,B}$. This leads to different oscillation frequencies for the two masses even if $D_{H,C}=D_{H,B}$ and to an observable beat due to $D^{hom}$. The presence of a hetero-nuclear spin in one of the chemical groups but not the other lifts the magnetic equivalence between the two protons. If for simplicity, only one carbon $^{13}$C atom is considered as the group A, one obtains the molecular structure $^1$H—$^{13}$C—B—$^1$H (FIG. 11d, left). The two protons now exhibit two different hetero-nuclear J-coupling constants $J_{H,C}^{het}$, $J_{H,B,C}^{het}$ which modify the two proton frequencies even for vanishing chemical shift difference in ultra-low fields. Consequently, the homo-nuclear coupling with constant $J^{hom}$ is visible in ultra-low fields if $|J_{H,C}^{het}-J_{H,B,C}^{het}|\geqq|J^{hom}|$. Quantum mechanical calculations show, that this condition is valid for multi-spin systems in general, including all homo- and hetero-nuclear J-couplings. The expected spectrum (FIG. 11e) consists of two pairs of doublets grouped symmetrically around the frequencies $\omega_H$ with different hetero-nuclear J-coupling constants. Both the homo-nuclear and the hetero-nuclear J-coupling constants can now be measured in ultra-low field.

Now, we will discuss the following liquids which were investigated: tetramethylsilane (TMS) with $^{13}$C and silicon $^{29}$Si in natural abundance, and 99% $^{13}$C-enriched methanol. The sample preparation, the Earth's field NMR setup, the pre-polarization and the measurement procedure are described elsewhere [41].

To simulate the NMR spectra of a J-coupled N+1-spin system (N proton spins and one $^{13}$C spin) the time evolution of the initial density matrix under the influence of the N+1 spin Hamilton matrix was calculated numerically. The $2^{N+1}\times 2^{N+1}$ dimensional J-coupled Hamilton matrix is built up by the N proton spin operators and by one $^{13}$C spin operator, which are constructed by the direct product approach [42]. The free induction decay (FID) was obtained by calculating the trace of the total transverse proton spin multiplied with the density matrix. After Fourier transformation of the calculated FID the spectrum was phase corrected. A transverse relaxation time was introduced such that the essential spectral features are well resolved.

Figure 12:
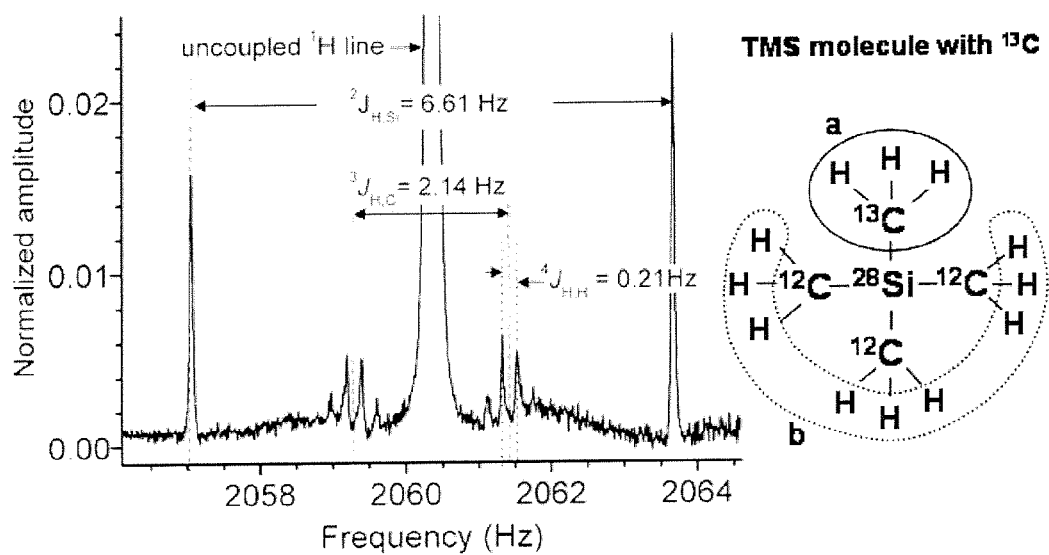
FIG. 12 is a $^1H$-NMR spectral of TMS substituted with a single $^{13}C$ atom.

A homo-nuclear J-coupling was observed for the first time in the Earth's field $^1$H-NMR spectrum of tetramethylsilane (TMS) in natural abundance. TMS has twelve protons, which are J-coupled to a silicon isotope $^{29}$Si (abundance f=0.047) or to $^{13}$C (f=0.01). The J-coupled $^1$H-NMR spectrum of TMS in FIG. 12 is dominated by the $^1$H—$^{29}$Si coupling. It shows an isolated central line at 2060.3 Hz with the normalized intensity $A_0=1$ and a $^1$H—$^{29}$Si J-coupled doublet with $^2J_{H,Si}=6.607$ Hz (the upper left index of the J-coupling constant denotes the number of chemical bonds between the coupled nuclei). The $^1$H—$^{29}$Si doublet has no substructure since all the hetero-nuclear $^1$H—$^{29}$Si J-coupling constants are exactly the same and obey the relation $|\omega_H-\omega_{Si}|>>2\pi|J_{H,Si}|$. Therefore, the twelve protons are all magnetically equivalent with respect to $^{29}$Si, and the homo-nuclear J-coupling constant $^4J_{H,H}$ is unobservable. But for the 1% of $^{13}$CH$_3$—Si—($^{12}$CH$_3$)$_3$ molecules, the situation is quite different. The three protons are coupled to $^{13}$C with the hetero-nuclear J-coupling constant $^1J_{Ha,C}=118$ Hz [41], which is different from the coupling constant of the nine protons coupled to $^{13}$C with $J_{Hb,C}=2.139$ Hz. This difference in hetero-nuclear $^1$H—$^{13}$C J-coupling constants breaks the magnetic equivalence between the three protons of the $^{13}$CH$_3$-group and the nine protons of the three $^{12}$CH$_3$-groups. Because in the Earth's field $|\psi_H-\omega_C|\geqq 2\pi|^1J_{Ha,C}|$ and $|^1J_{Ha,C}-^3J_{Hb,C}|>>|^4J_{Ha,Hb}|$, the expected $^1$H-TMS spectrum consists of a pair of quartets and a pair of forty lines. Indeed a close view of the TMS spectrum (FIG. 12) shows a pair of quartets with an 1:3:3:1 intensity ratio and which is grouped symmetrically around the uncoupled $^1$H-line. From the frequency separation between the two centres of each quartet structure $^3J_{Hb,C}=2.139$ Hz is determined. The frequency difference of two subsequent quartet lines is $^4J_{Ha,Hb}=0.209$ Hz. The intensity of the smallest quartet line is more than 1,000 times smaller than the intensity $A_0$ of the uncoupled protons.

The intensities of the multiplet lines can be estimated. We define M as the number of all proton spins, N as the number of proton spins of one group and M−N as the number of proton spins of the other group. If the M−N spins are observed, the intensity of the smallest line of the N+1 multiplet is given by $A_{N+1}=A_0\times f\times(\frac{1}{2})\times((M-N)/M)/2^N$. For TMS with M=12, N=3, f=0.01, and $A_0=1$ the intensity of the smallest quartet line is $A_4=5\times10^{-4}$, which is in agreement with the smallest quartet line of the TMS spectrum in FIG. 12.

The $^1$H-spectrum of the three protons of the $^{13}$CH$_3$-group splits first into a pair of four lines due to the strong coupling as $|\omega_H-\omega_C|=2\pi\times1542$ Hz$\approx 13\times 2\pi|^1J_{Ha,C}|$. The reason for the splitting into four lines will be explained in the next section. Due to the homo-nuclear J-coupling to the nine protons of the other three methyl groups, each of these four lines further splits into a multiplet with ten lines. The intensity of the smallest line of the M−N+1 multiplet, if the N spins are observed, is $A_{M-N+1}=A_0\times f\times(\frac{1}{2})\times(N/M)/2^{M-N}$. For TMS the result is $A_{10}=2\times10^{-6}$. The intensity of the smallest of the forty lines is given by $A_{40}=(\frac{1}{4})A_{10}\approx 5\times10^{-7}$ which cannot be measured with our spectrometer. In the corresponding high-field $^1$H-spectrum of TMS with a line width of about 1 Hz, the $^1$H—$^{29}$Si J-coupling constant is hardly resolved and the pair of quartets is hidden by the broad line of the uncoupled protons. At high field, a $^1$H—$^{13}$C J-coupled doublet with $^1J_{H,C}=118$ Hz is observed [41], but the complete structure consisting of a pair of multiplets with ten lines each spaced by 0.209 Hz is not resolved. Note that the Earth's field TMS spectrum yields more structural information than the high-field spectrum although no chemical shift information can be extracted from the ultra-low field $^1$H-spectrum.

Figure 13:
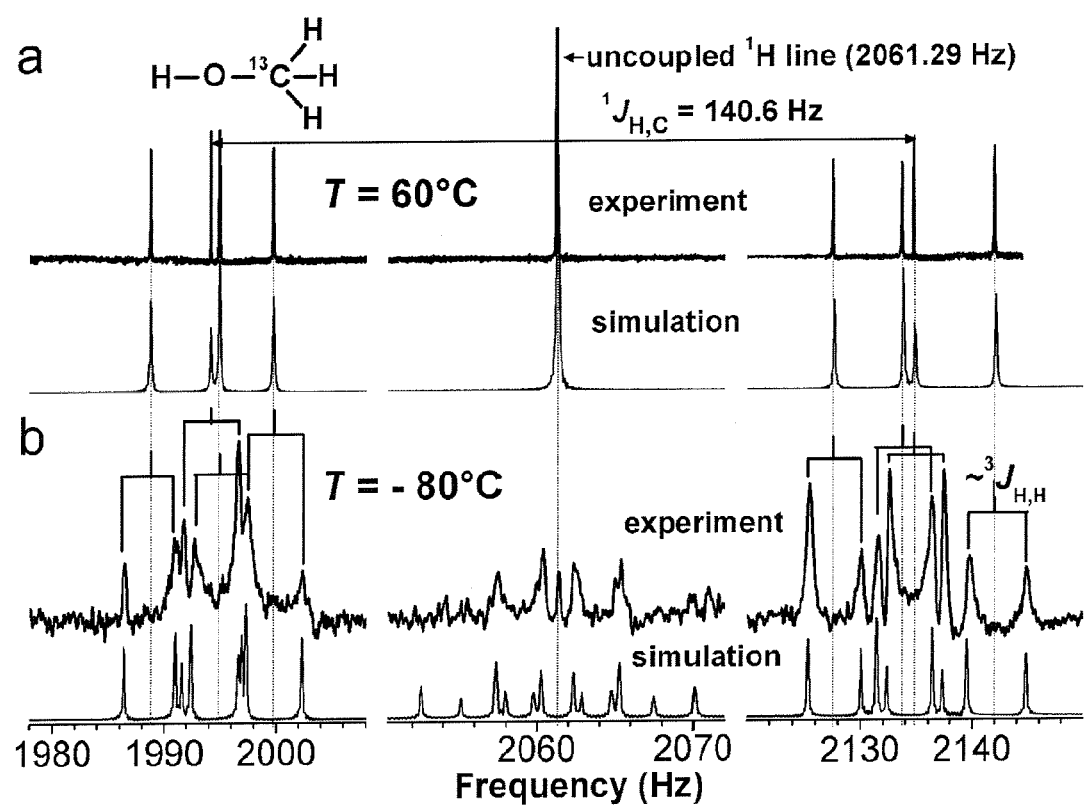
FIG. 13 includes experimental and simulated J-coupled $^1H$-spectra of 99% $^{13}C$ enriched methanol in Earth's magnetic field.

In FIG. 13 are shown the Earth's field $^1$H-spectra of $^{13}$C enriched methanol (f=0.99) measured at two different temperatures. At T=60° C. the OH-protons exchange rapidly (residence time τ<<0.1 s) between different molecules so that they do not experience any homo- or hetero-nuclear J-couplings. These uncoupled protons are visible in the $^1$H-spectrum by the central line at 2061.29 Hz in the top of FIG. 13a. Under the prevailing rapid exchange, the J-coupled Earth's field spectrum is one example of a strongly coupled four-spin system with three protons and one $^{13}$C, where $|\omega_H-\omega_C|\geq 2\pi|^1J_{H,C}|$. We observe a pair of multiplets with four lines each (FIG. 13a, top). The asymmetric pattern and the varying line spacing are in full agreement with the quantum mechanical calculation of the transverse $^1$H-magnetisation which evolves under the influence of the strongly coupled four-spin $^{13}$CH$_3$-Hamiltonian with $^1J_{H,C}$=140.6 Hz[44] (see FIG. 13a, bottom). We remark that the splitting is purely due to the strong hetero-nuclear $^1$H—$^{13}$C J-coupling in low field where the off-diagonal elements in the $^{13}$CH$_3$-Hamilton matrix are no longer small in the Zeeman eigen-basis compared to the differences of the corresponding diagonal elements. This leads to different shifts of the energy eigen-values and to a lift of the degeneracy of the two J-coupled lines. The number of four lines for each J-coupled line can be explained as follows: If we observe one proton of the $^{13}$CH$_3$-group, then the other two proton spins can group into either a triplet state with three possible orientations and into a singlet state with one possible orientation with respect to the magnetic field. This leads to a total of 1+3=4 lines with different frequencies. Although no proton chemical shift information is provided by the Earth's field spectrum, the chemical structure of the $^{13}$CH$_3$-group can be identified by the splitting into a pair of four lines. A similar phenomenon has been reported first by Benoit et al., who observed a pair of two lines for the strongly coupled PH$_2$-group in low field [39]. In general we found from simulations that for a strongly coupled YX$_N$-group (Y=spin ½, X=measured spin ½, N=natural number) one measures a pair of multiplets where the number K of lines of each multiplet is given by $$K = \sum_{n=1, n \in U}^{N} N - n + 1 \quad (1)$$

where U represents the set of odd numbers. In other words a strongly coupled $^{13}$CH$_N$-group for N=1, 2, 3, 4 can be identified in the ultra-low field spectrum as a pair of one, two, four, and six J-coupled lines, respectively.

At a temperature of T=−80° C. (FIG. 13b, top) the residence time of the OH-proton is long enough (τ>1 s) that the homo-nuclear J-coupling between the OH— and the $^{13}$CH$_3$-groups is not averaged out [45,46]. Now a five-spin system is observed for H—O—$^{13}$CH$_3$ under the condition of the two strong coupling limits, where $|\omega_H-\omega_C|\geq 2\pi|^1J_{H,C}|$ and $|^1J_{H,C}-^2J_{H,C}|\geq|^3J_{H,H}|$. The homo-nuclear J-coupling starts to be observable, and each of the four strongly coupled $^1$H-lines in the line groups of FIG. 13a splits into a doublet, resulting in an outer pair of eight lines each (FIG. 13b, top). The frequency separation between the lines of the doublets is approximately the homo-nuclear coupling constant $^3J_{H,H}$=5.0 Hz[44]. The observed outer pair with eight lines each is in full agreement with the quantum mechanical calculation as shown in the bottom of FIG. 13b, where the J-coupling constants have been assumed to be $^1J_{H,C}$=140.6 Hz, $^2J_{H,C}$=−2.4 Hz, and $^3J_{H,H}$=5.0 Hz [44,47]. The calculation also predict a pair of six observable transitions around the uncoupled $^1$H-line at 2061.29 Hz, as indicated in the bottom of FIG. 13b. The number of six lines is formally analogue to the strongly hetero-nuclear coupled $^{13}$CH$_4$-molecule but with the difference that now one OH-proton is strongly homo-nuclear J-coupled ($|^1J_{H,C}-^2J_{H,C}|\geq|^3J_{H,H}|$) to the other three protons of the $^{13}$CH$_3$-group. Note that a small peak at the frequency of the uncoupled $^1$H-line is visible in the experimental spectrum of FIG. 13b (but not in the simulated spectrum). This is due to the uncoupled $^1$H-signal of the 1% of methanol molecules containing $^{12}$C with no nuclear spin.

In summary, we have shown that valuable information about the molecular structure can be gained by NMR in ultra-low fields, where no chemical shift information is available. This is possible for two reasons: 1) A chemical group (e.g. $^{13}$CH$_3$) can be identified at ultra-low field because the strong hetero-nuclear coupling limit ($|\omega_H-\omega_C|\geq 2\pi|^1J_{H,C}|$) applies, leading to a characteristic hetero-nuclear splitting of the $^1$H-resonance into a pair of multiplets. 2) If two or more different chemical groups constitute the molecule, and one of them contains a rare spin, e.g. a $^{13}$C-nucleus, then the homo- and hetero-nuclear coupling network can be observed as multiplet pairs. The underlying mechanism for the multiplets to arise is that the magnetic equivalence between the protons of different chemical groups is lifted by the presence of different hetero-nuclear J-couplings from the protons of different chemical groups to the rare spin. Although at low field, the complexity of the spectra of larger molecules with rare spins in natural abundance is high, we can use the spectral pattern as a fingerprint of the molecular structure. As a consequence not only molecular structures but also dynamic processes, such as the intermolecular $^1$H-exchange can be studied in ultra-low magnetic fields with high precision.

Figure 11:
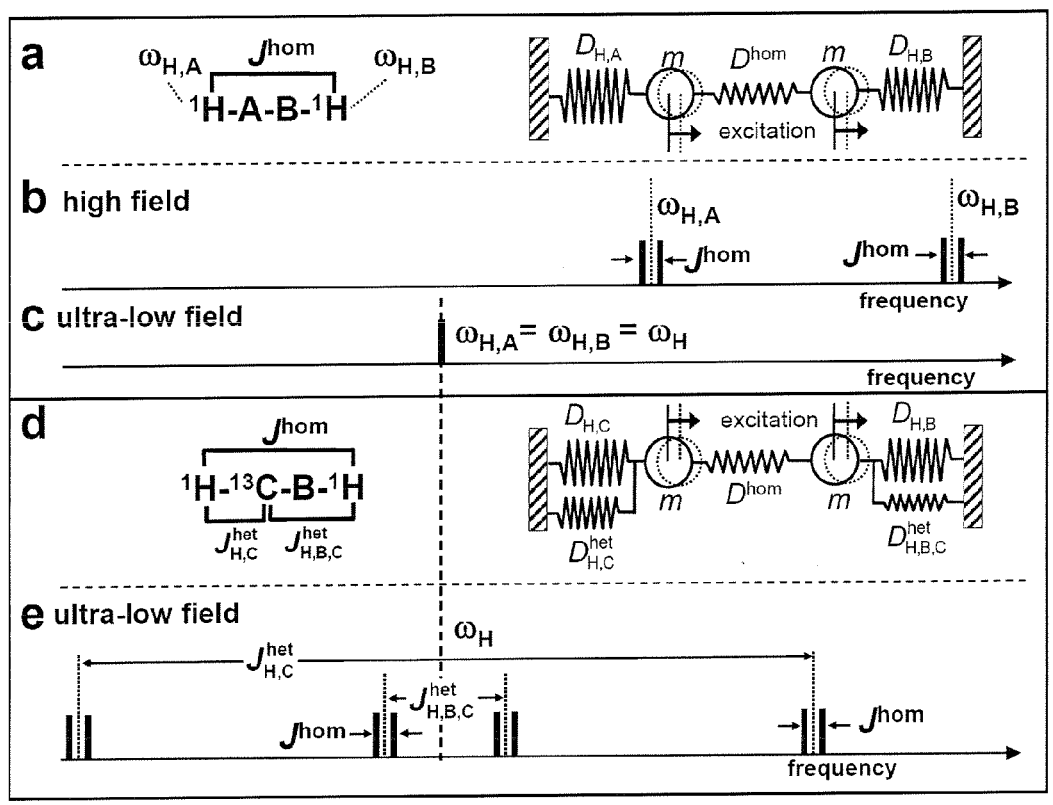
FIG. 11 demonstrates the principles of homonuclear and heteronuclear J-couplings in high and ultra-low strength magnetic fields.

Figure Legends concerning FIGS. 11 to 13:

FIG. 11. Mechanical analogon of J-coupled $^1$H-NMR. (a) Bead-and-spring model (right) of two spins $^1$H-A-B—$^1$H (left) interacting through the homo-nuclear J-coupling with coupling constant $J^{hom}$ via the chemical groups A and B. $D_{H,A}$, $D_{H,B}$, and $D^{hom}$ denote the corresponding spring constants, and m is the mass of the two coupled mechanical oscillators. If $D_{H,A}=D_{H,B}$, then $D^{hom}$ cannot be measured. The corresponding high field (b) and ultra-low field spectra (c) are sketched as stick spectra (d). Three-spin system $^1$H—$^{13}$C—B—$^1$H (left) and corresponding mechanical analogon (right). $J_{H,C}^{het}$ and $J_{H,B,C}^{het}$ are two different hetero-nuclear J-coupling constants, which correspond to $D_{H,C}^{het}$ and $D_{H,B,C}^{het}$ in the bead-and-spring model. Note, that $D^{hom}$ can be measured even if $D_{H,C}=D_{H,B}$. e, Corresponding stick spectrum in ultra-low field showing all three homo- and hetero-nuclear J-couplings.

FIG. 12. J-coupled Earth's field $^1$H-spectrum of tetramethylsilane (TMS). Nine scans at T=60° C. have been averaged. The line of the uncoupled protons with the transition frequency 2060.3 Hz (B$_0$=4.8391×10$^{-5}$ T) is normalised to one. The doublet with $^2J_{H,Si}$=6.607 Hz corresponds to the hetero-nuclear $^1$H—$^{29}$Si J-coupling originating from TMS molecules containing $^{29}$Si but no $^{13}$C. An additional pair of quartets separated by the hetero-nuclear J-coupling constant $^3J_{Hb,C}$=2.139 Hz appears with a homo-nuclear J-coupling constant $^4J_{Hb,Ha}$=0.209 Hz originating from TMS molecules containing $^{13}$C but no $^{29}$Si. The line width of each quartet line is about 0.05 Hz.

FIG. 13. Experimental and simulated J-coupled Earth's field $^1$H-spectra of 99% $^{13}$C enriched methanol. All experimental spectra are averages of nine scans. The line width of all simulated lines is 0.16 Hz ($T_2$=2 s). (a) The $^1$H-spectrum (top) measured at T=60° C. shows a pair of four unevenly spaced lines. The line width of the experimental J-coupled lines is about 0.07 Hz. The simulation of the spectrum is shown in the bottom. (b) $^1$H spectrum (top) measured at T=−80° C. The homo-nuclear J-coupling between the protons of the OH— and the $^{13}$CH$_3$-group is observable due to slow intermolecular $^1$H-exchange. The line width of the J-coupled lines is about 0.6 Hz. The simulated spectrum of the five-spin system HO—$^{13}$CH$_3$ is shown in the bottom.

REFERENCES

[1] R. R. Ernst, G. Bodenhausen, A. Wokaun, *Principles of Nuclear Magnetic Resonance in One and Two Dimensions*, Clarendon Press, Oxford, UK, 1987.

[2]. J. Jeener, B. H. Meier, Bachmann, P. & Ernst R. R. Investigation of exchange processes by two-dimensional NMR spectroscopy. *J. Chem. Phys.* 71, 4546-4553 (1979).

[3] W. G. Proctor, F. C. Yu, Phys. Rev. 81 (1951) 20.

[4] W. G. Proctor, F. C. Yu, *Phys. Rev.* 77 (1950) 717.

[5]. Arnold, J. T., Dharmatti, S. S. & Packard, M. E. Chemical Effects on Nuclear Induction Signals from Organic Compounds. *J. Chem. Phys.* 19, 507 (1951).

[6] M. A. Bouchiat, T. R. Carver, C. M. Varnum, Phys. Rev. Lett. 5 (1960) 373.

[7] Colegrove, F. D., Schearer, L. D. & Walters, G. K. Polarization of $^3$He Gas by Optical Pumping. *Phys. Rev.* 132, 2561-2572 (1963).

[8] W. Happer, Rev. Mod. Phys. 44 (1972) 169.

[9] B. Driehuys, G. D. Cates, E. Miron, K. Sauer, D. K. Walter, W. Happer, Appl. Phys. Lett. 69 (1996) 1668.

[10] S. Appelt, A. Ben-Amar Baranga, C. J. Erickson, M. V. Romalis, A. R. Young, W. Happer, Phys. Rev. A 58, (1998) 1412.

[11] C. R. Bowers, D. P. Weitekamp, Phys. Rev. Lett. 57 (1986) 2645.

[12] M. Goldman, H. Jóhannesson, O. Axelsson, M. Karlsson, Magn. Reson. Imag. 23 (2005) 153.

[13] G. Navon, Y.-Q. Song, T. Rõõm, S. Appelt, R. E. Taylor, A. Pines, Science 271 (1996) 1848.

[14] S. Appelt, F. W. Häsing, S. Baer-Lang, N. J. Shah, B. Blümich, Chem. Phys. Lett. 348 (2001) 263.

[15] Y. S. Greenberg, Rev. Mod. Phys. 70 (1998) 175.

[16] McDermott, R. et al. Liquid-State NMR and Scalar Couplings in Microtesla Magnetic Fields. *Science* 295, 2247-2249 (2002).

[17] Trabesinger, A. H. et al., SQUID-Detected Liquid State NMR in Microtesla Fields. *J. Phys. Chem. A* 108, 957-963 (2004).

[18] Bernarding, J. et al J-Coupling Nuclear Magnetic Resonance Spectroscopy of Liquids in nT Fields. *J. Am. Chem. Soc.* 128, 714-715 (2006).

[19] I. K. Kominis, T. W. Kornack, J. C. Allred, M. V. Romalis, Nature 422 (2003) 596.

[20] I. M. Savukov, M. V. Romalis, Phys. Rev. Lett. 94 (2005) 123001.

[21] Savukov, I. M., Lee, S.-K. & Romalis, M. V. Optical detection of liquid-state NMR. *Nature* 442, 1021-1024 (2006).

[22] C. A. Meriles, D. Sakellariou, D. H. Heise, A. J. Moulé, A. Pines, Science 293 (2001) 82.

[23] J. Perlo, V. Demas, F. Casanova, C. A. Meriles, J. Reimer, A. Pines, B. Blümich, Science 308 (2005) 1279.

[24] S. Appelt, F. W. Häsing, H. Kühn, J. Perlo, B. Blümich, Phys. Rev. Lett. 94 (2005) 197602.

[25] M. Packard, R. Varian, Phys. Rev. 93 (1954) 941.

[26] Melton, B. F. & Pollak, V. L. Instrumentation for the Earth's Field NMR Technique. *Rev. Sci. Instrum.* 42, 769-773 (1971).

[27] A. Shushakov, Geophysics 61 (1996) 998.

[28] R. J. S. Brown, Conc. Magn. Reson. 13 (2001) 344.

Béné, G. J., Borcard, B., Hiltbrand, É. & Magnin, P. in *NMR in Medicine* (ed. Damadian, R.) 81-99 (Springer, Berlin, 1981).

[30] Goedecke, R. & von Boetticher, H. Erdfeld-NMR: Apparative Entwicklungen zur In-vivo-Analyse von Körperflüssigkeiten und weichem Gewebe. *Z. Med. Phys.* 9, 130-138 (1999).

[31] Stepišnik, J., Kos, M., Planinšič, G. & Eržen, V. Strong Nonuniform Magnetic Field for Self-Diffusion Measurement by NMR in the Earth's Magnetic Field. *J. Magn. Reson. A* 107, 167-172 (1994).

[32] Belorizky, E. et al. Translational Diffusion Constants and Intermolecular Relaxation in Paramagnetic Solutions with Hyperfine Coupling on the Electronic Site. *J. Phys. Chem. A* 102, 3674-3680 (1998).

[33] Planinšič, G., Stepišnik, J. & Kos, M. Relaxation-Time Measurement and Imaging in the Earth's Magnetic Field. *J. Magn. Reson. A* 110, 170-174 (1994).

[34] Robinson, J. N. et al. Two-dimensional NMR spectroscopy in Earth's magnetic field. *J. Magn. Reson.* 182, 343-347 (2006).

[35] M. E. Halse, A. Coy, R. Dykstra, C. Eccles, M. Hunter, R. Ward, P. T. Callaghan, J. Magn. Reson. 182 (2006) 75.

[36] P. T. Callaghan, C. D. Eccles, J. D. Seymour, Rev. Sci. Instrum. 68 (1997) 4263.

[37] Callaghan, P. T., Dykstra, R., Eccles, C. D., Haskell, T. G. & Seymour, J. D. A nuclear magnetic resonance study of Antarctic sea ice brine diffusivity. *Cold Regions Science and Technology* 29, 153 (1999).

[38] Mercier, O. R., Hunter, M. W. & Callaghan, P. T. Brine diffusion in first-year sea ice measured by Earth's field PGSE-NMR. *Cold Regions Science and Technology* 42, 96-105 (2005).

[39] H. Benoit, J. Hennequin, H. Ottavi, Chimie Analytique 44 (1962) 471.

[40] G. J. Béné, Phys. Rep. 58 (1980) 213.

[41] S. Appelt, H. Kühn, F. W. Häsing, B. Blümich, Nat. Phys. 2 (2006) 105.

[42] P. J. Hore, J. A. Jones, S. Wimperis, *NMR: The Toolkit*, Oxford University Press, 2000.

[43] Burghoff, M., Hartwig, S., Trahms, L. & Bernarding, J. Nuclear magnetic resonance in the nanoTesla range. *Appl. Phys. Lett.* 87, 054103 (2005).

[44] F. A. Bovey, *NMR Data Tables for Organic Compounds*, Wiley Interscience Publishers, New York, 1967.

[45] E. Grunwald, C. F. Jumper, S. Meiboom, J. Am. Chem. Soc. 84 (1962) 4664.

[46] Farrar, T. C., Wendt, M. A. & Zeidler, M. D. Oxygen-17-induced Proton Relaxation Rates for Alcohols and Alcohol Solutions. *J. Braz. Chem. Soc.* 10, 321-325 (1999).

[47] M. Pecul, T. Helgaker, Int. J. Mol. Sci. 4 (2003) 143.

The invention claimed is:

1. A method for examining a sample by nuclear magnetic resonance spectroscopy, comprising
   measuring, in a magnetic field weaker than $10^{-3}$ Tesla, homonuclear J-couplings of atoms in the sample, and
   characterizing the sample based on the measured homonuclear couplings.

2. The method of claim 1, wherein the sample volume is 0.1 to 4 cm$^3$.

3. The method of claim 1, wherein the sample is pre-magnetized in a magnetic field having a strength of at least 0.1 Tesla.

4. The method of claim 1, wherein the sample includes organic molecules.

5. The method of claim 1, wherein the samples include molecules having the structure $X^M$-A-B—$X^K$, wherein X represents a magnetically active atom, A and B are any arbitrary molecular groups, and M and K are positive integers.

6. The method of claim 1, wherein measuring the homonuclear J-couplings comprises measuring $^1$H—$^1$H J-couplings.

7. The method of claim 1, wherein the sample includes atoms such that at least two different heteronuclear J-couplings result therefrom.

8. The method of claim 1, wherein the magnetic field is weaker than $10^{-4}$ Tesla.

9. The method of claim 1, further comprising measuring heteronuclear J-couplings of the sample and characterizing the sample therefrom.

10. The method of claim 1, further comprising pre-magnetizing the sample by hyperpolarizing the nuclear spin of the sample.

11. The method of claim 1, further comprising continuously irradiating the sample with radio frequency radiation during measurement of a proton spectrum, wherein the radiated frequency is significantly different from the $^1$H Larmor frequency of the sample.

12. A method of examining a sample by nuclear magnetic resonance (NMR) spectroscopy, comprising
measuring, in a magnetic field weaker than $5 \times 10^{-3}$ T, homonuclear and heteronuclear J-couplings of sample molecules, and
determining the sample molecular structure from an associated multiplet structure resulting from the resonance of molecules in the sample.

13. The method of claim 12, wherein the NMR spectrometer including the $B_0$ field causes an instrumental line broadening that is much smaller than the natural line width of the measured nucleus.

14. The method of claim 12, wherein the NMR spectrometer is sufficiently sensitive to measure, with a sufficient signal-to-noise ratio, the small intensities of the multiplet structures.

15. The method of claim 12, wherein the volume of the sample is 0.1 to 4 cm$^3$.

16. The method of claim 12, further comprising pre-magnetizing the sample in a magnetic field having a strength of at least 0.1 Tesla.

17. The method of claim 12, wherein the sample includes atoms such that at least two different heteronuclear J-couplings result therefrom.

18. The method of claim 12, wherein the samples include molecules having the structure $X^M$-A-B—$X^K$, wherein X represents a magnetically active atom, A and B are any arbitrary molecular groups, and M and K are positive integers.

19. The method of claim 12, wherein the magnetic field is weaker than $10^{-4}$ Tesla.

20. The method of claim 12, wherein the nuclear spins to be measured are polarized by a hyperpolarization technology selected from the group consisting of spin-exchange optical pumping, PHIP, DNP and combinations thereof.

21. The method of claim 18, further comprising continuously irradiating the sample with radio frequency radiation during measurement such that the irradiated frequency is in resonance with the coupled heteronuclear nucleus in the group A or B and is sufficiently different from the frequency of the X nucleus that no interference with the measurement occurs.

22. An apparatus for carrying out the method of claim 21, comprising
a polarizer for polarizing the sample, the polarizer including a transmitter coil for exciting the sample,
a magnetic field generator for generating a magnetic field having a homogeneity of better than 1 ppm over 1 cm$^3$ over one hour, and
a magnetic screening having a screening factor of at least 5000.

* * * * *